United States Patent
Bellanca et al.

(10) Patent No.: US 8,882,508 B2
(45) Date of Patent: Nov. 11, 2014

(54) UNIVERSAL SCANNING MEMBER FOR USE ON DENTAL IMPLANT AND DENTAL IMPLANT ANALOGS

(75) Inventors: John J. Bellanca, West Palm Beach, FL (US); Brandt M. Davis, Palm Beach Gardens, FL (US); Alexis C. Goolik, Denver, CO (US); David Edward Beeby, Wotton-Under-Edge (GB)

(73) Assignee: Biomet 3i, LLC, Palm Beach Gardens, FL (US)

( * ) Notice: Subject to any disclaimer, the term of this patent is extended or adjusted under 35 U.S.C. 154(b) by 125 days.

(21) Appl. No.: 13/312,900

(22) Filed: Dec. 6, 2011

(65) Prior Publication Data
US 2012/0141951 A1 Jun. 7, 2012

Related U.S. Application Data

(60) Provisional application No. 61/420,541, filed on Dec. 7, 2010.

(51) Int. Cl.
*A61C 8/00* (2006.01)
*A61C 9/00* (2006.01)

(52) U.S. Cl.
CPC ............ *A61C 8/0001* (2013.01); *A61C 9/0093* (2013.01)
USPC .......................................... 433/214; 433/172

(58) Field of Classification Search
USPC .......................... 433/172, 173, 174, 213, 214
See application file for complete search history.

(56) References Cited

U.S. PATENT DOCUMENTS

| | | | |
|---|---|---|---|
| 3,906,634 A | 9/1975 | Aspel | |
| 3,919,772 A | 11/1975 | Lenczycki | |
| 3,958,471 A | 5/1976 | Muller | |
| 4,011,602 A | 3/1977 | Rybicki et al. | |
| 4,056,585 A | 11/1977 | Waltke | |
| 4,086,701 A | 5/1978 | Kawahara et al. | |

(Continued)

FOREIGN PATENT DOCUMENTS

| | | | | |
|---|---|---|---|---|
| DE | 10029256 | 11/2000 | ............... | A61C 1/08 |
| DE | 20 2010 017228 | 5/2011 | ............... | A61C 8/00 |

(Continued)

OTHER PUBLICATIONS

Biomet 3i—Manual entitled "Navigator™ System for CT Guided Surgery Manual", Revision A 10/07—34 pages.
Brochure: NobelProcera™ and Procera™ Abutment Titanium and Zirconia. Nobel Biocare™, Mar. 15, 2010, 10 pages.

(Continued)

*Primary Examiner* — Ralph Lewis
(74) *Attorney, Agent, or Firm* — Nixon Peabody LLP

(57) ABSTRACT

A scanning member includes a head portion and a body portion. The head portion has an at least partially flat top surface indicative of a first characteristic of a dental implant, an at least partially flat first side surface indicative of a second characteristic of the dental implant, and a second non-flat side surface that opposes the first side surface. The body portion has a non-rotational feature configured to non-rotationally couple the body portion to the dental implant. The body portion is physically attached to a bottom surface of the head portion to form a generally "T" shape. The scanning member has an internal through hole for receiving a screw to threadably couple with a threaded bore within the dental implant. A set of scanning members includes scanning members having different body portions configured to couple to dental implants from different manufacturers.

22 Claims, 9 Drawing Sheets

(56) References Cited

U.S. PATENT DOCUMENTS

| | | |
|---|---|---|
| 4,177,562 A | 12/1979 | Miller et al. |
| 4,294,544 A | 10/1981 | Altschuler et al. |
| 4,306,862 A | 12/1981 | Knox |
| 4,325,373 A | 4/1982 | Slivenko et al. |
| 4,341,312 A | 7/1982 | Scholer |
| 4,364,381 A | 12/1982 | Sher et al. |
| 4,439,152 A | 3/1984 | Small |
| 4,543,953 A | 10/1985 | Slocum et al. |
| 4,547,157 A | 10/1985 | Driskell |
| 4,571,180 A | 2/1986 | Kulick |
| 4,611,288 A | 9/1986 | Duret et al. |
| 4,624,673 A | 11/1986 | Meyer |
| 4,663,720 A | 5/1987 | Duret et al. |
| 4,713,004 A | 12/1987 | Linkow et al. |
| 4,756,689 A | 7/1988 | Lundgren |
| 4,758,161 A | 7/1988 | Niznick |
| 4,767,331 A | 8/1988 | Hoe |
| 4,772,204 A | 9/1988 | Soderberg |
| 4,821,200 A | 4/1989 | Öberg |
| 4,842,518 A | 6/1989 | Linkow et al. |
| 4,850,870 A | 7/1989 | Lazzara et al. |
| 4,850,873 A | 7/1989 | Lazzara et al. |
| 4,854,872 A | 8/1989 | Detsch |
| 4,856,994 A | 8/1989 | Lazzara et al. |
| 4,872,839 A | 10/1989 | Brajnovic |
| 4,906,191 A | 3/1990 | Soderberg |
| 4,906,420 A | 3/1990 | Brajnovic |
| 4,931,016 A | 6/1990 | Sillard |
| 4,935,635 A | 6/1990 | O'Harra |
| 4,961,674 A | 10/1990 | Wang et al. |
| 4,964,770 A | 10/1990 | Steinbichler et al. |
| 4,986,753 A | 1/1991 | Sellers |
| 4,988,297 A | 1/1991 | Lazzara et al. |
| 4,988,298 A | 1/1991 | Lazzara et al. |
| 4,998,881 A | 3/1991 | Lauks |
| 5,000,685 A | 3/1991 | Brajnovic |
| 5,006,069 A | 4/1991 | Lazzara et al. |
| 5,015,183 A | 5/1991 | Fenick |
| 5,015,186 A | 5/1991 | Detsch |
| 5,030,096 A | 7/1991 | Hurson et al. |
| 5,035,619 A | 7/1991 | Daftary |
| 5,040,982 A | 8/1991 | Stefan-Dogar |
| 5,040,983 A | 8/1991 | Binon |
| 5,064,375 A | 11/1991 | Jörneus |
| 5,071,351 A | 12/1991 | Green, Jr. et al. |
| 5,073,111 A | 12/1991 | Daftary |
| 5,087,200 A | 2/1992 | Brajnovic et al. |
| 5,100,323 A | 3/1992 | Friedman et al. |
| 5,104,318 A | 4/1992 | Piche et al. |
| 5,106,300 A | 4/1992 | Voitik |
| 5,122,059 A | 6/1992 | Dürr et al. |
| 5,125,839 A | 6/1992 | Ingber et al. |
| 5,125,841 A | 6/1992 | Carlsson et al. |
| 5,133,660 A | 7/1992 | Fenick |
| 5,135,395 A | 8/1992 | Marlin |
| 5,145,371 A | 9/1992 | Jörnéus |
| 5,145,372 A | 9/1992 | Daftary et al. |
| 5,176,516 A | 1/1993 | Koizumi |
| 5,188,800 A | 2/1993 | Green, Jr. et al. |
| 5,195,892 A | 3/1993 | Gersberg |
| 5,205,745 A | 4/1993 | Kamiya et al. |
| 5,209,659 A | 5/1993 | Friedman et al. |
| 5,209,666 A | 5/1993 | Balfour et al. |
| 5,213,502 A | 5/1993 | Daftary |
| 5,237,998 A | 8/1993 | Duret et al. |
| 5,246,370 A | 9/1993 | Coatoam |
| 5,257,184 A | 10/1993 | Mushabac |
| 5,281,140 A | 1/1994 | Niznick |
| 5,286,195 A | 2/1994 | Clostermann |
| 5,286,196 A | 2/1994 | Brajnovic et al. |
| 5,292,252 A | 3/1994 | Nickerson et al. |
| 5,297,963 A | 3/1994 | Dafatry |
| 5,302,125 A | 4/1994 | Kownacki et al. |
| 5,312,254 A | 5/1994 | Rosenlicht |
| 5,312,409 A | 5/1994 | McLaughlin et al. |
| 5,316,476 A | 5/1994 | Krauser |
| 5,320,529 A | 6/1994 | Pompa |
| 5,328,371 A | 7/1994 | Hund et al. |
| 5,334,024 A | 8/1994 | Niznick |
| 5,336,090 A | 8/1994 | Wilson, Jr. et al. |
| 5,338,196 A | 8/1994 | Beaty et al. |
| 5,338,198 A | 8/1994 | Wu et al. |
| 5,343,391 A | 8/1994 | Mushabac |
| 5,344,457 A | 9/1994 | Pilliar et al. |
| 5,350,297 A | 9/1994 | Cohen |
| 5,359,511 A | 10/1994 | Schroeder et al. |
| 5,362,234 A | 11/1994 | Salazar et al. |
| 5,362,235 A | 11/1994 | Daftary |
| 5,368,483 A | 11/1994 | Sutter et al. |
| 5,370,692 A | 12/1994 | Fink |
| 5,372,502 A | 12/1994 | Massen et al. |
| 5,386,292 A | 1/1995 | Massen et al. |
| 5,413,481 A | 5/1995 | Göppel et al. |
| 5,417,569 A | 5/1995 | Perisse |
| 5,417,570 A | 5/1995 | Zuest et al. |
| 5,419,702 A | 5/1995 | Beaty et al. |
| 5,431,567 A | 7/1995 | Datary |
| 5,437,551 A | 8/1995 | Chalifoux |
| 5,440,393 A | 8/1995 | Wenz |
| 5,452,219 A | 9/1995 | Dehoff et al. |
| 5,458,488 A | 10/1995 | Chalifoux |
| 5,476,382 A | 12/1995 | Daftary |
| 5,476,383 A | 12/1995 | Beaty et al. |
| 5,492,471 A | 2/1996 | Singer |
| 5,516,288 A | 5/1996 | Sichler et al. |
| 5,527,182 A | 6/1996 | Willoughby |
| 5,533,898 A | 7/1996 | Mena |
| 5,538,426 A | 7/1996 | Harding et al. |
| 5,547,377 A | 8/1996 | Daftary |
| 5,556,278 A | 9/1996 | Meitner |
| 5,564,921 A | 10/1996 | Marlin |
| 5,564,924 A | 10/1996 | Kwan |
| 5,569,578 A | 10/1996 | Mushabac |
| 5,575,656 A | 11/1996 | Hajjar |
| 5,580,244 A | 12/1996 | White |
| 5,580,246 A | 12/1996 | Fried |
| 5,595,703 A | 1/1997 | Swaelens et al. |
| 5,613,832 A | 3/1997 | Su |
| 5,613,852 A | 3/1997 | Bavitz |
| 5,630,717 A | 5/1997 | Zuest |
| 5,636,986 A | 6/1997 | Pezeshkian |
| 5,651,675 A | 7/1997 | Singer |
| 5,652,709 A | 7/1997 | Andersson et al. |
| 5,658,147 A | 8/1997 | Phimmasone |
| 5,662,476 A | 9/1997 | Ingber et al. |
| 5,674,069 A | 10/1997 | Osorio |
| 5,674,071 A | 10/1997 | Beaty et al. |
| 5,674,073 A | 10/1997 | Ingber et al. |
| 5,681,167 A | 10/1997 | Lazarof |
| 5,685,715 A | 11/1997 | Beaty et al. |
| 5,688,283 A | 11/1997 | Knapp |
| 5,704,936 A | 1/1998 | Mazel |
| 5,718,579 A | 2/1998 | Kennedy |
| 5,725,376 A | 3/1998 | Poirier |
| 5,733,124 A | 3/1998 | Kwan |
| 5,741,215 A | 4/1998 | D'Urso |
| 5,743,916 A | 4/1998 | Greenberg et al. |
| 5,759,036 A | 6/1998 | Hinds |
| 5,762,125 A | 6/1998 | Mastrorio |
| 5,762,500 A | 6/1998 | Lazarof |
| 5,768,134 A | 6/1998 | Swaelens et al. |
| 5,769,636 A | 6/1998 | Di Sario |
| 5,791,902 A | 8/1998 | Lauks |
| 5,800,168 A | 9/1998 | Cascione et al. |
| 5,813,858 A | 9/1998 | Singer |
| 5,823,778 A | 10/1998 | Schmitt et al. |
| 5,842,859 A | 12/1998 | Palacci |
| 5,846,079 A | 12/1998 | Knode |
| 5,851,115 A | 12/1998 | Carlsson et al. |
| 5,857,853 A | 1/1999 | Van Nifterick et al. |
| 5,871,358 A | 2/1999 | Ingber et al. |
| 5,873,722 A | 2/1999 | Lazzara et al. |
| 5,876,204 A | 3/1999 | Day et al. |
| 5,885,078 A | 3/1999 | Cagna et al. |

(56) References Cited

U.S. PATENT DOCUMENTS

| | | |
|---|---|---|
| 5,888,034 A | 3/1999 | Greenberg |
| 5,904,483 A | 5/1999 | Wade |
| 5,915,962 A | 6/1999 | Rosenlicht |
| 5,927,982 A | 7/1999 | Kruger |
| 5,938,443 A | 8/1999 | Lazzara et al. |
| 5,954,769 A | 9/1999 | Rosenlicht |
| 5,964,591 A | 10/1999 | Beaty et al. |
| 5,967,777 A | 10/1999 | Klein et al. |
| 5,984,681 A | 11/1999 | Huang |
| 5,989,025 A | 11/1999 | Conley |
| 5,989,029 A | 11/1999 | Osorlo |
| 5,989,258 A | 11/1999 | Hattori |
| 5,997,681 A | 12/1999 | Kinzie |
| 6,000,939 A | 12/1999 | Ray et al. |
| 6,008,905 A | 12/1999 | Breton et al. |
| 6,068,479 A | 5/2000 | Kwan |
| 6,099,311 A | 8/2000 | Wagner et al. |
| 6,099,313 A | 8/2000 | Dorken et al. |
| 6,099,314 A | 8/2000 | Kopelman et al. |
| 6,120,293 A | 9/2000 | Lazzara et al. |
| 6,129,548 A | 10/2000 | Lazzara et al. |
| 6,135,773 A | 10/2000 | Lazzara |
| 6,142,782 A | 11/2000 | Lazarof |
| 6,174,168 B1 | 1/2001 | Dehoff et al. |
| 6,175,413 B1 | 1/2001 | Lucas |
| 6,190,169 B1 | 2/2001 | Bluemli et al. |
| 6,197,410 B1 | 3/2001 | Vallittu et al. |
| 6,200,125 B1 | 3/2001 | Akutagawa |
| 6,206,693 B1 | 3/2001 | Hultgren |
| 6,210,162 B1 | 4/2001 | Chishti |
| 6,217,334 B1 | 4/2001 | Hultgren |
| 6,227,859 B1 | 5/2001 | Sutter |
| 6,283,753 B1 | 9/2001 | Willoughby |
| 6,287,119 B1 | 9/2001 | van Nifterick |
| 6,296,483 B1 | 10/2001 | Champleboux |
| 6,319,000 B1 | 11/2001 | Branemark |
| 6,322,728 B1 | 11/2001 | Brodkin |
| 6,382,975 B1 | 5/2002 | Poirier |
| 6,402,707 B1 | 6/2002 | Ernst |
| 6,488,503 B1 | 12/2002 | Lichkus et al. |
| 6,497,574 B1 | 12/2002 | Miller |
| 6,540,784 B2 | 4/2003 | Barlow |
| 6,568,936 B2 | 5/2003 | MacDougald |
| 6,575,751 B1 | 6/2003 | Lehmann et al. |
| 6,594,539 B1 | 7/2003 | Geng |
| 6,610,079 B1 | 8/2003 | Li |
| 6,619,958 B2 | 9/2003 | Beaty et al. |
| 6,629,840 B2 | 10/2003 | Chishti |
| 6,634,883 B2 | 10/2003 | Ranalli |
| 6,648,640 B2 | 11/2003 | Rubbert et al. |
| 6,671,539 B2 | 12/2003 | Gateno et al. |
| 6,672,870 B2 | 1/2004 | Knapp |
| 6,688,887 B2 | 2/2004 | Morgan |
| 6,691,764 B2 | 2/2004 | Embert |
| 6,743,491 B2 | 6/2004 | Cirincione et al. |
| 6,755,652 B2 | 6/2004 | Nanni |
| 6,772,026 B2 | 8/2004 | Bradbury |
| 6,776,614 B2 | 8/2004 | Wiechmann et al. |
| 6,783,359 B2 | 8/2004 | Kapit |
| 6,790,040 B2 | 9/2004 | Amber et al. |
| 6,793,491 B2 | 9/2004 | Klein et al. |
| 6,808,659 B2 | 10/2004 | Schulman |
| 6,814,575 B2 | 11/2004 | Poirier |
| 6,821,462 B2 | 11/2004 | Schulamn et al. |
| 6,829,498 B2 | 12/2004 | Kipke et al. |
| D503,804 S | 4/2005 | Phleps et al. |
| 6,882,894 B2 | 4/2005 | Durbin et al. |
| 6,885,464 B1 | 4/2005 | Pfeiffer et al. |
| 6,902,401 B2 | 6/2005 | Jorneus et al. |
| 6,913,463 B2 | 7/2005 | Blacklock |
| 6,926,442 B2 | 8/2005 | Stöckl |
| 6,926,525 B1 | 8/2005 | Ronvig |
| 6,939,489 B2 | 9/2005 | Moszner et al. |
| 6,942,699 B2 | 9/2005 | Stone et al. |
| 6,953,383 B2 | 10/2005 | Rothenberger |
| 6,957,118 B2 | 10/2005 | Kopelman et al. |
| 6,966,772 B2 | 11/2005 | Malin et al. |
| 6,970,760 B2 | 11/2005 | Wolf et al. |
| 6,971,877 B2 | 12/2005 | Harter |
| 6,994,549 B2 | 2/2006 | Brodkin et al. |
| 7,010,150 B1 | 3/2006 | Pfeiffer et al. |
| 7,010,153 B2 | 3/2006 | Zimmermann |
| 7,012,988 B2 | 3/2006 | Adler et al. |
| 7,018,207 B2 | 3/2006 | Prestipino |
| 7,021,934 B2 | 4/2006 | Aravena |
| 7,029,275 B2 | 4/2006 | Rubbert et al. |
| 7,044,735 B2 | 5/2006 | Malin |
| 7,056,115 B2 | 6/2006 | Phan et al. |
| 7,056,472 B1 | 6/2006 | Behringer |
| 7,059,856 B2 | 6/2006 | Marotta |
| 7,066,736 B2 | 6/2006 | Kumar et al. |
| 7,084,868 B2 | 8/2006 | Farag et al. |
| 7,086,860 B2 | 8/2006 | Schuman et al. |
| 7,097,451 B2 | 8/2006 | Tang |
| 7,104,795 B2 | 9/2006 | Dadi |
| 7,110,844 B2 | 9/2006 | Kopelman |
| 7,112,065 B2 | 9/2006 | Kopelman |
| 7,118,375 B2 | 10/2006 | Durbin et al. |
| D532,991 S | 12/2006 | Gozzi |
| 7,153,132 B2 | 12/2006 | Tedesco |
| 7,153,135 B1 | 12/2006 | Thomas |
| 7,163,443 B2 | 1/2007 | Basler et al. |
| 7,175,434 B2 | 2/2007 | Brajnovic |
| 7,175,435 B2 | 2/2007 | Andersson et al. |
| 7,178,731 B2 | 2/2007 | Basler |
| 7,214,062 B2 | 5/2007 | Morgan |
| 7,220,124 B2 | 5/2007 | Taub et al. |
| 7,228,191 B2 | 6/2007 | Hofmeister et al. |
| 7,236,842 B2 | 6/2007 | Kopelman et al. |
| 7,281,927 B2 | 10/2007 | Marotta |
| 7,286,954 B2 | 10/2007 | Kopelman et al. |
| 7,303,420 B2 | 12/2007 | Huch et al. |
| 7,319,529 B2 | 1/2008 | Babayoff |
| 7,322,746 B2 | 1/2008 | Beckhaus et al. |
| 7,322,824 B2 | 1/2008 | Schmitt |
| 7,324,680 B2 | 1/2008 | Zimmermann |
| 7,329,122 B1 | 2/2008 | Scott |
| 7,333,874 B2 | 2/2008 | Taub et al. |
| 7,335,876 B2 | 2/2008 | Eiff et al. |
| D565,184 S | 3/2008 | Royzen |
| 7,367,801 B2 | 5/2008 | Saliger |
| 7,379,584 B2 | 5/2008 | Rubbert et al. |
| D571,471 S | 6/2008 | Stöckl |
| 7,381,191 B2 | 6/2008 | Fallah |
| 7,383,094 B2 | 6/2008 | Kopelman et al. |
| D575,747 S | 8/2008 | Abramovich et al. |
| 7,421,608 B2 | 9/2008 | Schron |
| 7,425,131 B2 | 9/2008 | Amber et al. |
| 7,429,175 B2 | 9/2008 | Gittelson |
| 7,435,088 B2 | 10/2008 | Brajnovic |
| 7,476,100 B2 | 1/2009 | Kuo |
| 7,481,647 B2 | 1/2009 | Sambu et al. |
| 7,488,174 B2 | 2/2009 | Kopelman et al. |
| 7,497,619 B2 | 3/2009 | Stoeckl |
| 7,497,983 B2 | 3/2009 | Khan et al. |
| 7,520,747 B2 | 4/2009 | Stonisch |
| 7,522,764 B2 | 4/2009 | Schwotzer |
| 7,534,266 B2 | 5/2009 | Kluger |
| 7,536,234 B2 | 5/2009 | Kopelman et al. |
| 7,545,372 B2 | 6/2009 | Kopelman et al. |
| 7,551,760 B2 | 6/2009 | Scharlack et al. |
| 7,555,403 B2 | 6/2009 | Kopelman et al. |
| 7,556,496 B2 | 7/2009 | Cinader, Jr. et al. |
| 7,559,692 B2 | 7/2009 | Beckhaus et al. |
| 7,563,397 B2 | 7/2009 | Schulman et al. |
| D597,769 S | 8/2009 | Richter et al. |
| 7,572,058 B2 | 8/2009 | Pruss et al. |
| 7,572,125 B2 | 8/2009 | Brajnovic |
| 7,574,025 B2 | 8/2009 | Feldman |
| 7,578,673 B2 | 8/2009 | Wen et al. |
| 7,580,502 B2 | 8/2009 | Dalpiaz et al. |
| 7,581,951 B2 | 9/2009 | Lehmann et al. |
| 7,582,855 B2 | 9/2009 | Pfeiffer |
| 7,628,537 B2 | 12/2009 | Schulze-Ganzlin |

(56) References Cited

U.S. PATENT DOCUMENTS

| | | | |
|---|---|---|---|
| 7,632,097 B2 | 12/2009 | Clerck | |
| 7,653,455 B2 | 1/2010 | Cnader, Jr. et al. | |
| 7,654,823 B2 | 2/2010 | Dadi | |
| 7,655,586 B1 | 2/2010 | Brodkin et al. | |
| 7,658,610 B2 | 2/2010 | Knopp | |
| 7,661,956 B2 | 2/2010 | Powell et al. | |
| 7,665,989 B2 | 2/2010 | Brajnovic et al. | |
| 7,679,723 B2 | 3/2010 | Schwotzer | |
| 7,687,754 B2 | 3/2010 | Eiff et al. | |
| 7,689,308 B2 | 3/2010 | Holzner et al. | |
| D614,210 S | 4/2010 | Basler et al. | |
| 7,698,014 B2 | 4/2010 | Dunne et al. | |
| 7,774,084 B2 | 8/2010 | Cinader, Jr. | |
| 7,780,907 B2 | 8/2010 | Schmidt et al. | |
| 7,785,007 B2 | 8/2010 | Stoeckl | |
| 7,787,132 B2 | 8/2010 | Körner et al. | |
| 7,796,811 B2 | 9/2010 | Orth et al. | |
| 7,798,708 B2 | 9/2010 | Erhardt et al. | |
| 7,801,632 B2 | 9/2010 | Orth et al. | |
| 7,815,371 B2 | 10/2010 | Schulze-Ganzlin | |
| 7,824,181 B2 | 11/2010 | Sers | |
| D629,908 S | 12/2010 | Jerger et al. | |
| 7,855,354 B2 | 12/2010 | Eiff | |
| 7,865,261 B2 | 1/2011 | Pfeiffer | |
| 7,876,877 B2 | 1/2011 | Stockl | |
| 7,901,209 B2 | 3/2011 | Saliger et al. | |
| 7,982,731 B2 | 7/2011 | Orth et al. | |
| 7,985,119 B2 | 7/2011 | Basler et al. | |
| 7,986,415 B2 | 7/2011 | Thiel et al. | |
| 7,988,449 B2 * | 8/2011 | Amber et al. | 433/213 |
| 8,011,925 B2 | 9/2011 | Powell et al. | |
| 8,038,440 B2 | 10/2011 | Swaelens et al. | |
| 8,047,895 B2 | 11/2011 | Basler | |
| 8,057,912 B2 | 11/2011 | Basler et al. | |
| 8,062,034 B2 | 11/2011 | Hanisch et al. | |
| 2001/0008751 A1 | 7/2001 | Chishti et al. | |
| 2001/0034010 A1 | 10/2001 | MacDougald et al. | |
| 2002/0010568 A1 | 1/2002 | Rubbert et al. | |
| 2002/0028418 A1 | 3/2002 | Farag et al. | |
| 2002/0160337 A1 | 10/2002 | Klein et al. | |
| 2002/0167100 A1 | 11/2002 | Moszner | |
| 2003/0130605 A1 | 7/2003 | Besek | |
| 2003/0222366 A1 | 12/2003 | Stangel | |
| 2004/0029074 A1 | 2/2004 | Brajnovic | |
| 2004/0048227 A1 | 3/2004 | Brajnovic | |
| 2004/0219477 A1 | 11/2004 | Harter | |
| 2004/0219479 A1 | 11/2004 | Malin et al. | |
| 2004/0219490 A1 | 11/2004 | Gartner et al. | |
| 2004/0220691 A1 | 11/2004 | Hofmeister et al. | |
| 2004/0243481 A1 | 12/2004 | Bradbury et al. | |
| 2004/0259051 A1 | 12/2004 | Brajnovic | |
| 2005/0023710 A1 | 2/2005 | Brodkin et al. | |
| 2005/0056350 A1 | 3/2005 | Dolabdjian et al. | |
| 2005/0070782 A1 | 3/2005 | Brodkin | |
| 2005/0084144 A1 | 4/2005 | Feldman | |
| 2005/0100861 A1 | 5/2005 | Choi et al. | |
| 2005/0170311 A1 | 8/2005 | Tardieu et al. | |
| 2005/0271996 A1 | 12/2005 | Sporbert et al. | |
| 2005/0277089 A1 | 12/2005 | Brajnovic | |
| 2005/0277090 A1 | 12/2005 | Anderson et al. | |
| 2005/0277091 A1 | 12/2005 | Andersson et al. | |
| 2005/0282106 A1 | 12/2005 | Sussman et al. | |
| 2005/0283065 A1 | 12/2005 | Babayoff | |
| 2006/0006561 A1 | 1/2006 | Brajnovic | |
| 2006/0008763 A1 | 1/2006 | Brajnovic | |
| 2006/0008770 A1 | 1/2006 | Brajnovic et al. | |
| 2006/0072810 A1 | 4/2006 | Scharlack | |
| 2006/0093988 A1 | 5/2006 | Swaelens et al. | |
| 2006/0094951 A1 | 5/2006 | Dean et al. | |
| 2006/0127848 A1 | 6/2006 | Sogo et al. | |
| 2006/0210949 A1 | 9/2006 | Stoop | |
| 2006/0263741 A1 | 11/2006 | Imgrund et al. | |
| 2006/0281041 A1 | 12/2006 | Rubbert et al. | |
| 2007/0015111 A1 | 1/2007 | Kopelman et al. | |
| 2007/0031790 A1 | 2/2007 | Raby et al. | |
| 2007/0065777 A1 | 3/2007 | Becker | |
| 2007/0077532 A1 | 4/2007 | Harter | |
| 2007/0092854 A1 | 4/2007 | Powell et al. | |
| 2007/0141525 A1 | 6/2007 | Cinader, Jr. | |
| 2007/0211081 A1 | 9/2007 | Quadling et al. | |
| 2007/0218426 A1 | 9/2007 | Quadling et al. | |
| 2007/0269769 A1 | 11/2007 | Marchesi | |
| 2007/0281277 A1 | 12/2007 | Brajnovic | |
| 2008/0038692 A1 | 2/2008 | Andersson et al. | |
| 2008/0044794 A1 | 2/2008 | Brajnovic | |
| 2008/0057467 A1 | 3/2008 | Gittelson | |
| 2008/0070181 A1 | 3/2008 | Abolfathi et al. | |
| 2008/0085489 A1 | 4/2008 | Schmitt | |
| 2008/0090210 A1 | 4/2008 | Brajnovic | |
| 2008/0114371 A1 | 5/2008 | Kluger | |
| 2008/0118895 A1 | 5/2008 | Brajnovic | |
| 2008/0124676 A1 | 5/2008 | Marotta | |
| 2008/0153061 A1 | 6/2008 | Marcello | |
| 2008/0153065 A1 | 6/2008 | Brajnovic et al. | |
| 2008/0153067 A1 | 6/2008 | Berckmans et al. | |
| 2008/0153069 A1 | 6/2008 | Holzner et al. | |
| 2008/0176188 A1 * | 7/2008 | Holzner et al. | 433/215 |
| 2008/0176189 A1 | 7/2008 | Stonisch | |
| 2008/0206714 A1 | 8/2008 | Schmitt | |
| 2008/0241798 A1 | 10/2008 | Holzner et al. | |
| 2008/0261165 A1 | 10/2008 | Steingart et al. | |
| 2008/0300716 A1 | 12/2008 | Kopelman et al. | |
| 2009/0017418 A1 | 1/2009 | Gittelson | |
| 2009/0026643 A1 | 1/2009 | Wiest et al. | |
| 2009/0042167 A1 | 2/2009 | Van Der Zel | |
| 2009/0081616 A1 | 3/2009 | Pfeiffer | |
| 2009/0087817 A1 | 4/2009 | Jansen et al. | |
| 2009/0098510 A1 | 4/2009 | Zhang | |
| 2009/0098511 A1 | 4/2009 | Zhang | |
| 2009/0123045 A1 | 5/2009 | Quadling et al. | |
| 2009/0123887 A1 | 5/2009 | Brajnovic | |
| 2009/0187393 A1 | 7/2009 | Van Lierde et al. | |
| 2009/0220916 A1 | 9/2009 | Fisker et al. | |
| 2009/0220917 A1 | 9/2009 | Jensen | |
| 2009/0239197 A1 | 9/2009 | Brajnovic | |
| 2009/0239200 A1 | 9/2009 | Brajnovic et al. | |
| 2009/0253097 A1 | 10/2009 | Brajnovic | |
| 2009/0287332 A1 | 11/2009 | Adusumilli et al. | |
| 2009/0298009 A1 | 12/2009 | Brajnovic | |
| 2009/0298017 A1 | 12/2009 | Boerjes et al. | |
| 2009/0317763 A1 | 12/2009 | Brajnovic | |
| 2009/0325122 A1 | 12/2009 | Brajnovic et al. | |
| 2010/0009314 A1 | 1/2010 | Tardieu et al. | |
| 2010/0028827 A1 | 2/2010 | Andersson et al. | |
| 2010/0038807 A1 | 2/2010 | Brodkin et al. | |
| 2010/0075275 A1 | 3/2010 | Brajnovic | |
| 2010/0092904 A1 | 4/2010 | Esposti et al. | |
| 2010/0173260 A1 | 7/2010 | Sogo et al. | |
| 2010/0280798 A1 | 11/2010 | Pattijn et al. | |
| 2010/0296710 A1 * | 11/2010 | Schneider et al. | 382/128 |
| 2011/0008751 A1 | 1/2011 | Pettersson | |
| 2011/0191081 A1 | 8/2011 | Malfliet et al. | |
| 2011/0200970 A1 | 8/2011 | Berckmans et al. | |
| 2011/0244426 A1 | 10/2011 | Amber et al. | |
| 2011/0275032 A1 | 11/2011 | Tardieu et al. | |
| 2012/0010740 A1 | 1/2012 | Swaelens et al. | |

FOREIGN PATENT DOCUMENTS

| | | | |
|---|---|---|---|
| WO | WO 94/26200 | 11/1994 | A61C 8/00 |
| WO | WO 99/32045 | 7/1999 | A61C 1/08 |
| WO | WO 00/08415 | 2/2000 | A61B 5/107 |
| WO | WO 01/58379 | 8/2001 | A61C 15/02 |
| WO | WO 02/053055 | 7/2002 | A61C 8/00 |
| WO | WO 03/024352 | 3/2003 | A61C 8/00 |
| WO | WO 2004/030565 | 4/2004 | A61C 13/00 |
| WO | WO 2004/075771 | 9/2004 | A61C 13/00 |
| WO | WO 2004/087000 | 10/2004 | A61C 13/00 |
| WO | WO 2004/098435 | 11/2004 | A61C 1/08 |
| WO | WO 2006/014130 | 2/2006 | A61C 1/08 |
| WO | WO 2006/062459 | 6/2006 | A61C 3/02 |
| WO | WO 2006/082198 | 8/2006 | A61C 13/00 |
| WO | WO 2007/033157 | 3/2007 | A61C 5/00 |
| WO | WO 2007/104842 | 9/2007 | A61C 1/08 |

(56) References Cited

FOREIGN PATENT DOCUMENTS

| | | | |
|---|---|---|---|
| WO | WO 2007/129955 | 11/2007 | ............... A61C 8/00 |
| WO | WO 2008/057955 | 5/2008 | ............. A61C 19/00 |
| WO | WO 2008/083857 | 7/2008 | ............. A61C 13/00 |

OTHER PUBLICATIONS

Extended European Search Report and Opinion, EP Application No. 11191888.4, dated Mar. 22, 2012, 9 pages.

* cited by examiner

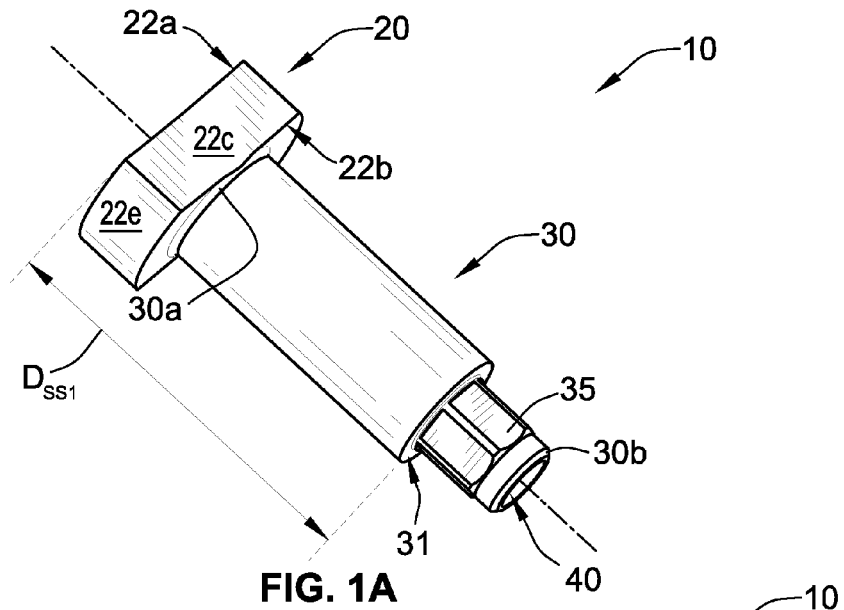
FIG. 1A
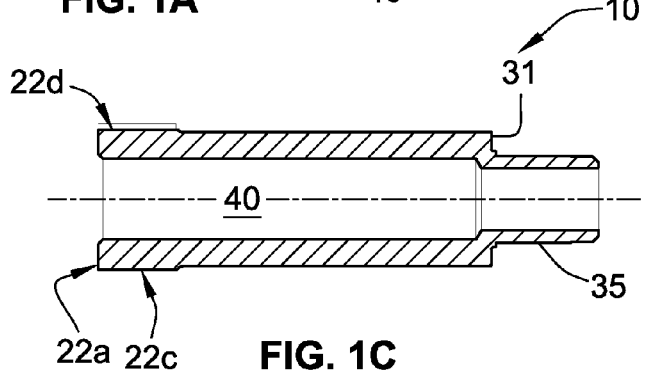
FIG. 1C
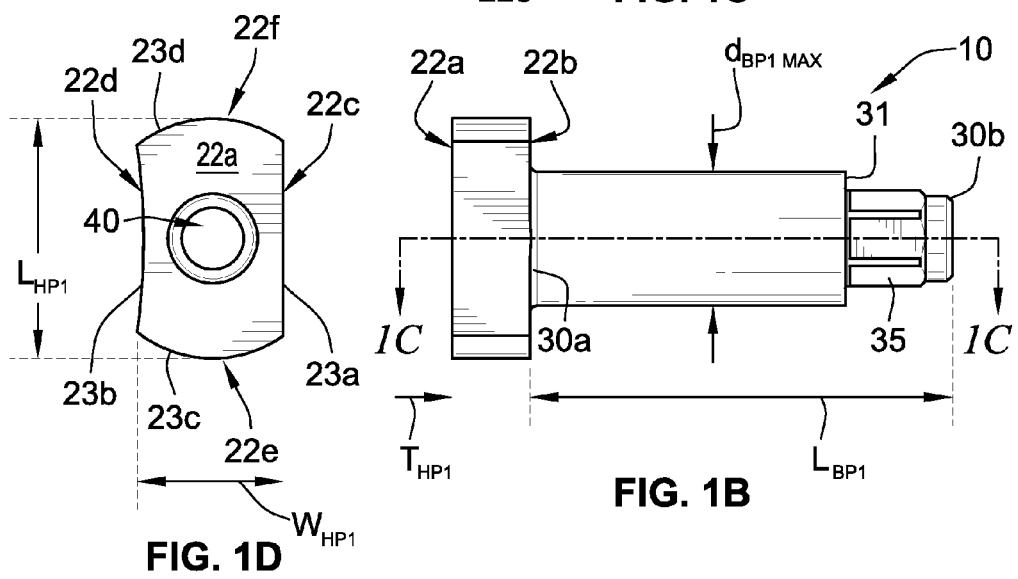
FIG. 1D
FIG. 1B

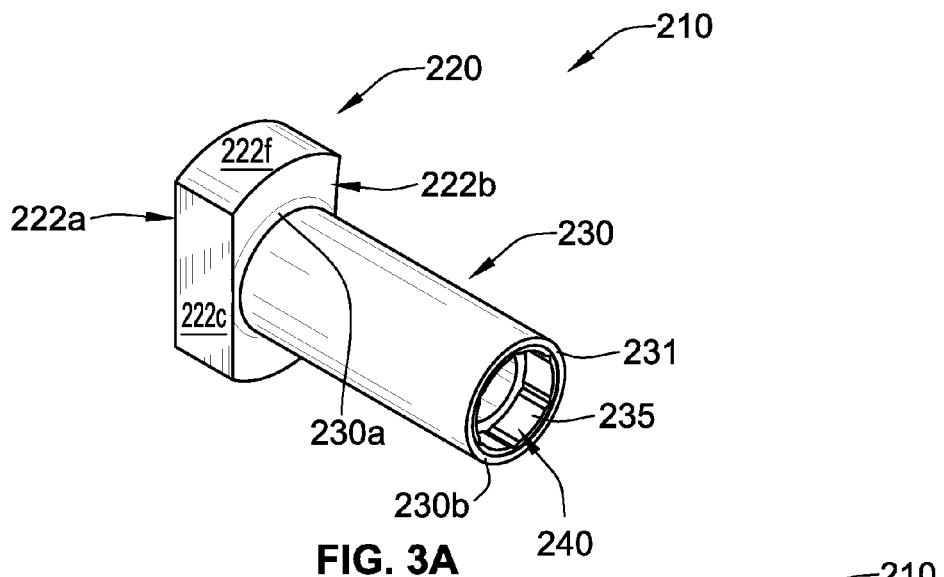
FIG. 3A
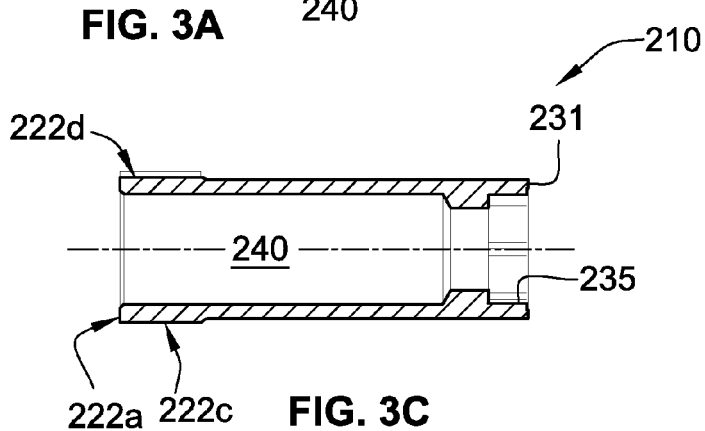
FIG. 3C
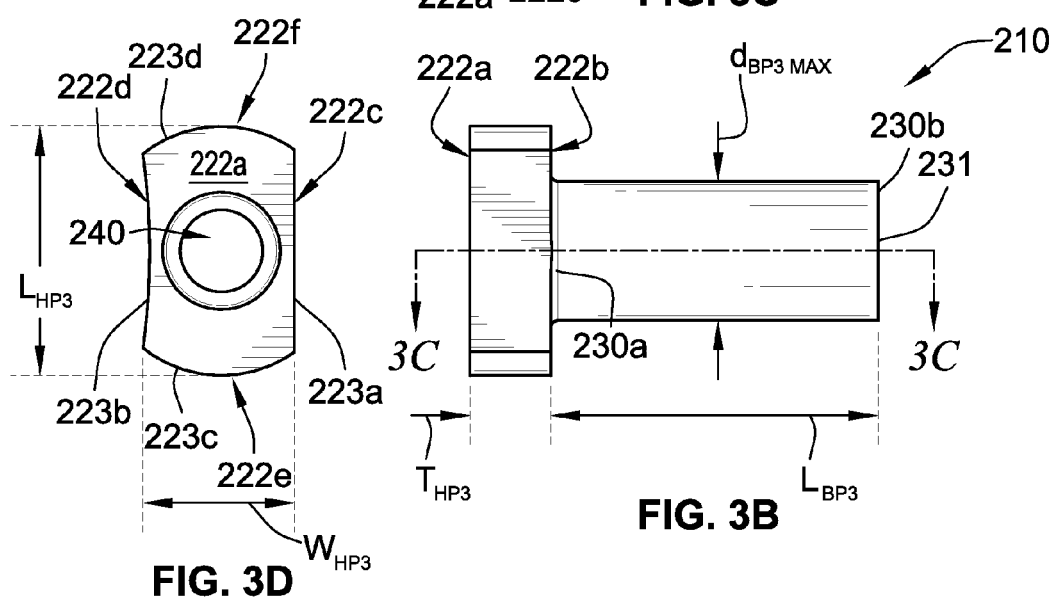
FIG. 3D
FIG. 3B

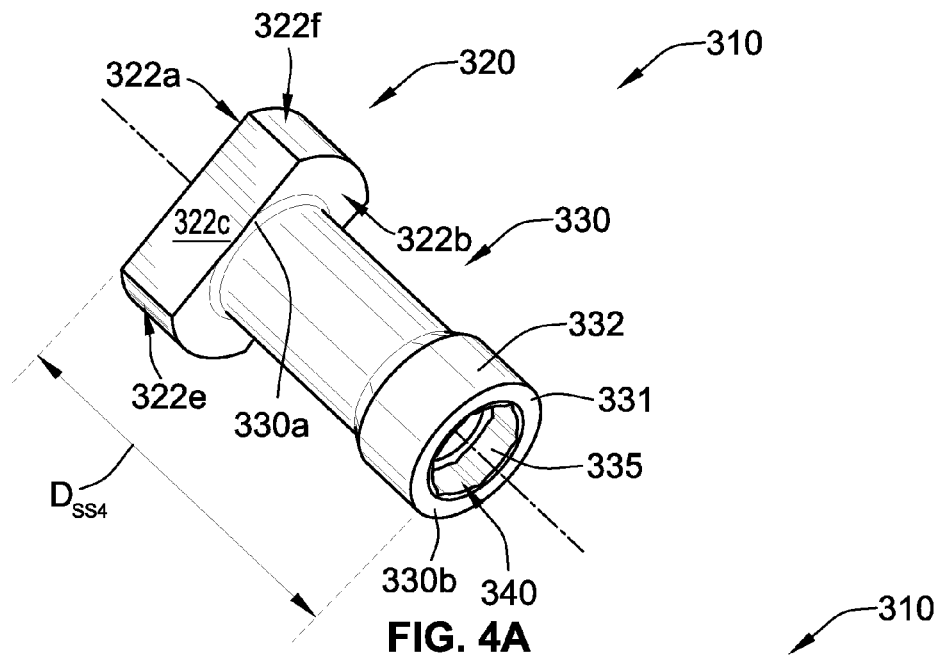
FIG. 4A
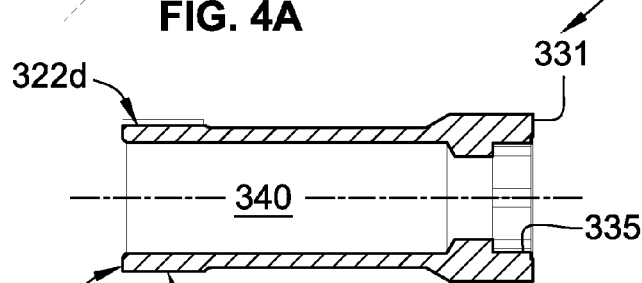
FIG. 4C
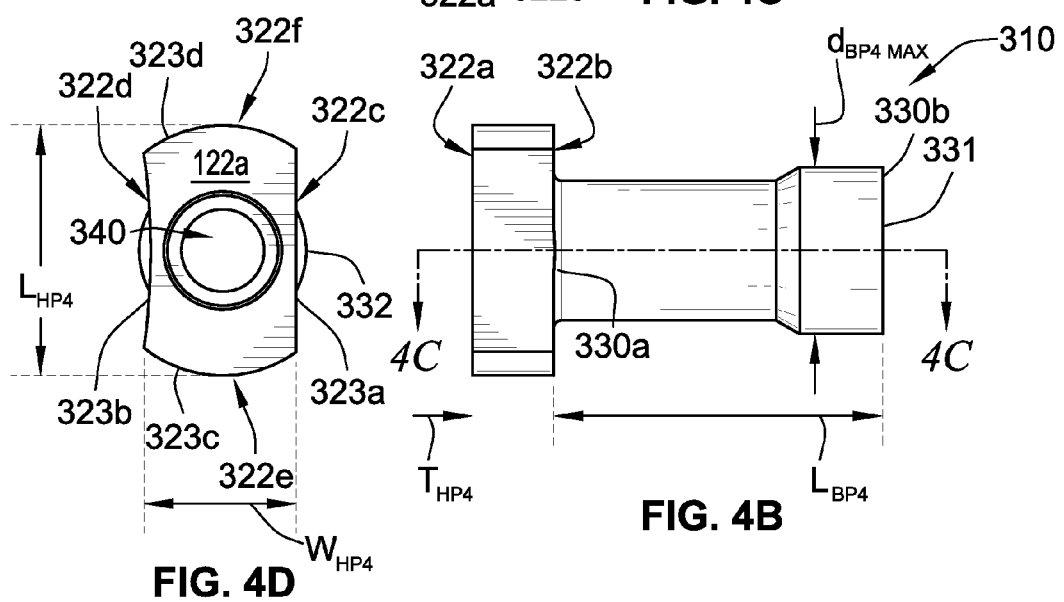
FIG. 4D
FIG. 4B

UNIVERSAL SCANNING MEMBER FOR USE ON DENTAL IMPLANT AND DENTAL IMPLANT ANALOGS

CROSS-REFERENCE TO RELATED APPLICATION

This application claims the benefit of U.S. Provisional Application No. 61/420,541, filed Dec. 7, 2010, which is incorporated by reference herein in its entirety.

FIELD OF THE INVENTION

The present disclosure relates generally to a scanning member in a dental implant system. More particularly, the present disclosure relates to the use of a scanning member to identify characteristics of a dental implant installed in a jawbone of a mouth.

BACKGROUND

The dental restoration of a partially or wholly edentulous patient with artificial dentition is typically done in two stages. In the first stage, an incision is made through the gingiva to expose the underlying bone. An artificial tooth root, in the form of a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the second stage is initiated. Here, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant preferably has a similar general contour as the gingival portion of the natural tooth being replaced. It should be noted that the healing abutment can be placed on the implant immediately after the implant has been installed and before osseointegration.

To develop a custom-abutment or tooth prosthesis, the location and orientation of the dental implant relative to adjacent teeth has been captured through the use of impression copings. While impression copings have been used in the past, modern dentistry has started to rely on scans of the mouth. The scans produce scan data that is typically analyzed to develop virtual three-dimensional models of the mouth, which is used in the production of the custom-abutment.

SUMMARY OF THE INVENTION

The present disclosure describes several types of scanning members and a set of scanning members. Each scanning member is configured to be coupled with a specific type and size of dental implant for use in developing a custom-abutment that is attached to the specific dental implant in the mouth of a patient. During the second stage of the dental restoration, the healing abutment is removed and one of the scanning members of the present disclosure is coupled with the exposed end of the dental implant. Each scanning member has a head portion physically attached to a body portion to form a generally "T" shape. Each head portion has a top surface indicative of a first characteristic of the specific dental implant and a first side surface indicative of a second characteristic of the specific dental implant. One of several scanning techniques is employed to determine the first and the second characteristics of the specific dental implants. The first and the second characteristics can be determined via a mechanical contact scanner and via an optical scanner, which can be employed for in-mouth optical scanning, optical model scanning (e.g., scanning of a stone or plaster model), and mechanical-contact model scanning. Once determined, the first and the second characteristics are used to develop the custom-abutment, which is attached to the dental implant. The head portions of the scanning members are substantially identical for all of the scanning members in the set.

A method of developing a custom-abutment for attachment to a dental implant in a mouth of a patient includes determining a type of the dental implant in the mouth of the patient. A scanning member is selected from a set of scanning members based on the determined type of the dental implant. Each of the scanning members in the set has a head portion coupled to a body portion. The head portions are identical for each of the scanning members in the set. The body portions are different for each of the scanning members in the set. Each of the body portions are configured to be coupled with a different type of non-rotational dental implant feature. The head portion has a top surface indicative of a first characteristic of the dental implant and a first side surface indicative of a second characteristic of the dental implant. The selected one of the scanning members is attached to the dental implant in the mouth of the patient. The first characteristic and the second characteristic of the dental implant are determined by scanning the head portion of the attached scanning member to gather information for manufacturing the custom-abutment. The custom abutment is developed based on the information from the first characteristic and the second characteristic of the attached scanning member.

A method of developing a custom-abutment for attachment to a dental implant in a mouth of a patient includes non-rotationally coupling a scanning member to the dental implant in the mouth of the patient. The scanning member has a head portion coupled to a body portion which forms a generally "T" shape. The head portion has a top surface indicative of a first characteristic of the dental implant and a first side surface indicative of a second characteristic of the dental implant. At least a portion of the mouth of the patient is scanned to create scan data. The portion of the mouth scanned includes the scanning member. The scan data is analyzed to determine the first characteristic and the second characteristic of the dental implant for use in manufacturing the custom-abutment. The custom abutment is developed based on the scan data, the first characteristic, and the second characteristic.

A set of scanning members includes a first scanning member and a second scanning member. The first scanning member has a first head portion coupled to a first body portion which forms a generally "T" shape. The first head portion has a first top surface indicative of a first characteristic of a first dental implant and a first side surface indicative of a second characteristic of the first dental implant. The first body portion is configured to be non-rotationally coupled to the first dental implant. The second scanning member has a second head portion coupled to a second body portion which forms a generally "T" shape. The second head portion has a second top surface indicative of a first characteristic of a second dental implant and a second side surface indicative of a second characteristic of the second dental implant. The second body portion is configured to be non-rotationally coupled to the second dental implant which is different than the first dental implant. The first and the second head portions are substantially identical.

A scanning member for use in developing a custom-abutment for attachment to a dental implant in a mouth of a patient includes a generally rectangular head portion and a body portion. The generally rectangular head portion has (i) a substantially-flat top surface indicative of a first characteristic of a dental implant configured to be coupled to the scanning member, (ii) a substantially-flat first side surface indicative of a second characteristic of the dental implant, the first side surface extending downward from the top surface towards a bottom surface of the head portion, and (iii) a curved second side surface that opposes the first side surface and extends downward from the top surface towards the bottom surface. The body portion has a non-rotational feature configured to non-rotationally couple the body portion to the dental implant. The body portion is physically attached to the bottom surface of the head portion to form a generally "T" shape. The scanning member has an internal through hole for receiving a screw to threadably couple with a threaded bore within the dental implant.

A method of manufacturing a custom dental abutment for mating with a dental implant includes scanning a model of a patient's dental conditions. The model includes a dental implant analog, teeth models, and a scanning member having a head portion coupled to a body portion. The scanning member has a generally "T" shape. The body portion is non-rotationally coupled to the dental implant analog. The head portion has a top surface indicative of a first characteristic of the dental implant analog and a first side surface indicative of a second characteristic of the dental implant analog. Scan data is generated from the scanning of the model. A virtual three-dimensional image is created of the patient's dental conditions with the scan data. The first characteristic and the second characteristic of the dental implant analog are determined to gather information for manufacturing the custom-abutment. Custom-abutment dimensional information is developed based on the virtual three-dimensional image and the information gathered. The custom-abutment is fabricated utilizing the custom-abutment dimensional information.

A set of scanning members includes a plurality of scanning members. Each of the scanning members has a head portion coupled to a body portion which forms a generally "T" shape. The head portions are configured to be scannable via a mechanical contact scanner and via an optical scanner to generate scan data for use in determining a first characteristic and a second characteristic of a dental implant.

BRIEF DESCRIPTION OF THE DRAWINGS

The foregoing and other advantages of the present disclosure will become apparent upon reading the following detailed description and upon reference to the drawings.

FIG. 1A is a perspective view of a scanning member according to the present disclosure;

FIG. 1B is a side view of the scanning member of FIG. 1A;

FIG. 1C is a cross-sectional side view of the scanning member of FIG. 1B;

FIG. 1D is a top view of the scanning member of FIG. 1A;

FIG. 3A is a perspective view of a third scanning member according to the present disclosure;

FIG. 3B is a side view of the scanning member of FIG. 3A;

FIG. 3C is a cross-sectional side view of the scanning member of FIG. 3B;

FIG. 3D is a top view of the scanning member of FIG. 3A;

FIG. 4A is a perspective view of a fourth scanning member according to the present disclosure;

FIG. 4B is a side view of the scanning member of FIG. 4A;

FIG. 4C is a cross-sectional side view of the scanning member of FIG. 4B;

FIG. 4D is a top view of the scanning member of FIG. 4A; and

Figure 1E:
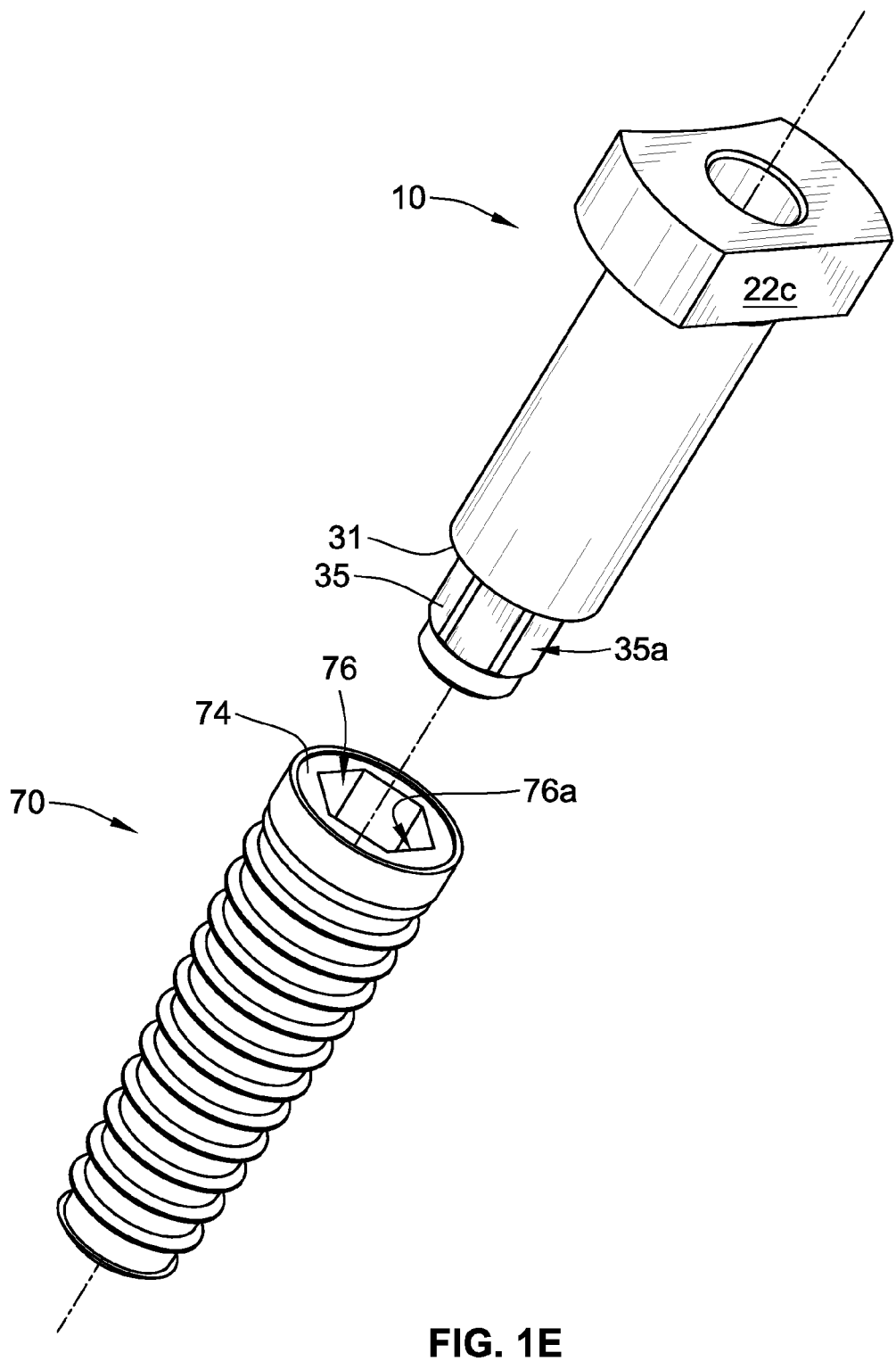
FIG. 1E is a perspective view of the scanning member of FIG. 1A aligned with a dental implant.

While the present disclosure is susceptible to various modifications and alternative forms, specific embodiments have been shown by way of example in the drawings and will be described in detail herein. It should be understood, however, that the present disclosure is not intended to be limited to the particular forms disclosed. Rather, the present disclosure is to cover all modifications, equivalents, and alternatives falling within the spirit and scope of the present disclosure as defined by the appended claims.

DESCRIPTION OF ILLUSTRATIVE EMBODIMENTS

The scanning members of the present disclosure can be used in two ways. First, the scanning members can be used directly in the mouth of a patient. In such a method, the scanning member is attached to a dental implant installed in the jawbone of the patient and scanned while in the mouth of the patient. Second, the scanning members can be used on a stone or plaster model of a mouth of a patient. In such a method, the scanning member is attached to a dental implant analog included in the model and scanned while on the model and not directly in the actual mouth of the patient. The context of each use will now be described.

During the first or second stage of dental restoration, a healing abutment (not shown) is non-rotationally fastened to a dental implant through complimentary non-round fittings or non-rotational features on the dental implant and healing abutment, which usually take the form of a polygonal shaped boss and polygonal shaped socket (e.g., hexagonal boss and hexagonal socket). The healing abutment is held on the dental implant via a screw that engages a threaded bore of the dental implant.

After a healing abutment is fastened to the exposed end of the dental implant and the gum tissue of the patient that underwent surgery heals therearound, one of a variety of scanning techniques can be employed to determine information used to develop a custom-abutment for attachment to the dental implant. Such scanning techniques include mechanical contact scanning, optical/image scanning, and laser scanning. All of these techniques can be applied to models of the mouth of the patient—which are typically stone models cast from impressions of the mouth—while the laser and optical scanning techniques can also be applied directly to the mouth of the patient.

In the case of a model being used, during the second stage of dental restoration, the healing abutment is removed and an impression coping is fitted onto the exposed end of the dental implant. This allows an impression of the specific region of the mouth of the patient to be taken so that an artificial tooth (e.g., a custom-abutment) is accurately constructed. Preferably, the impression coping has the same gingival dimensions as the healing element so that there is no gap between the impression coping and the wall of the gum tissue defining the aperture. Otherwise, a less than accurate impression of the condition of the mouth is taken. The impression coping may be a "pick-up"-type impression coping or a "transfer"-type impression coping. After the impression is made, a dental implant analog is attached to the impression via the impression coping and a stone or plaster model of the mouth is poured. When the model dries, the implant analog is set/secured in the model with the same orientation and location as the dental implant in the mouth of the patient.

A scanning member, according to aspects of the present disclosure, is then attached to the dental implant analog and the entire area is scanned using anyone of the scanning techniques mentioned herein or other techniques used to scan dentition models to generate scan data. After scanning, a laboratory can create and manufacture a prosthesis (custom-abutment), usually using a computer-aided design ("CAD") package, which uses the scan data generated from the scanning. The utilization of a CAD program, as disclosed in U.S. Pat. No. 5,338,198, whose disclosure is hereby incorporated by reference herein in its entirety, is one method of scanning a dental region to create a virtual three-dimensional model.

As mentioned above, the model can be laser scanned to create a virtual three-dimensional model of the patient's dentition. The model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known locations in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the generated scan data may be fed into a CAD system for manipulation of this electronic data by known means.

Similarly, optical scanning can be used to scan the model or directly in the mouth of the patient to create a virtual three-dimensional model of the patient's dentition. For example, one system takes photographs or optical images at multiple angles in one exposure to scan a dental region, create a virtual three-dimensional model, and manufacture a prosthetic tooth. As disclosed in U.S. Pat. No. 5,851,115, whose disclosure is hereby incorporated by reference herein in its entirety, this process is generally initiated with the process of taking a stereophotograph with a camera from approximately 50 to 150 mm away from the patient's mouth or model. The resulting photograph presents multiple images of the same object. The images on the photographs are scanned with a reading device that digitizes the photographs to produce a digital image of the dental region. The generated scan data from the scanner is electronically transmitted to a graphical imaging program that creates the virtual three-dimensional model.

A third scanning technique uses mechanical contact scanning to generate scan data. A mechanical contour sensing device, as disclosed in U.S. Pat. No. 5,652,709, whose disclosure is hereby incorporated by reference herein in its entirety, is another method used to scan a model for use in developing a prosthetic tooth. The model is secured to a table that may rotate about its longitudinal axis as well as translate along the same axis with variable speeds. A mechanical contact sensor is placed in contact with the model at a known angle and the sensing equipment is held firmly against the surface of the model by a spring. When the model is rotated and translated, the mechanical contact scanner measures the changes in the contour and generates scan data that can be used to create an electronic representation of the model (e.g., virtual three-dimensional model). One non-limiting example of a mechanical contact scanner suitable for use according to the present disclosure is a Series 2 RENISHAW® Dental Scanner sold by Renishaw plc of New Mills, Wotton-under-Edge, Gloucestershire, UK.

Regardless of the scanning technique employed to generate scan data, a computer and/or software program is able to receive the scan data and to create a virtual three-dimensional model of the relevant jaw section of the patient, including the dental implant and attached scanning member. Due to the shape and construction of the scanning member attached to the dental implant, or dental implant analog, the computer and/or software program is able to accurately analyze and produce the appropriate dimensions and location of the dental implant and an orientation of the underlying non-rotational feature of the dental implant so that a dentist or clinician can instruct a milling machine to produce a custom-abutment that is configured properly to attach to and align with the dental implant when installed in the mouth of the patient.

Referring to FIGS. 1A-1F, a scanning member 10 is shown according to aspects of the present disclosure. The scanning member 10 includes a head portion 20 and a body portion 30. The body portion 30 is physically attached to the head portion 20 to form a generally "T" shape. The head portion 20 of the scanning member 10 is configured to be scannable via a mechanical contact scanner, via an optical scanner, and a laser scanner to generate scan data for use in obtaining a first characteristic and a second characteristic of a dental implant (e.g., dental implant 70 in FIGS. 1E and 1F). These characteristics can be used in developing a custom abutment (not shown). That is, the scanning member 10 of the present disclosure can be used with the mechanical scanning techniques, with the optical scanning techniques, and/or with the laser scanning techniques described above.

The head portion 20 has a generally rectangular shape with six surfaces 22a-f. It is the specific shapes and orientations of these six surfaces 22a-f that configure the scanning member 10 to be scannable via mechanical, optical, and laser scanning techniques. The head portion 20 includes a top surface 22a, a bottom surface 22b that opposes the top surface 22a, a first side surface 22c, a second side surface 22d that opposes the first side surface 22c, a third side surface 22e, and a fourth side surface 22f that opposes the third side surface 22e. The third and the fourth side surfaces 22e,f are generally positioned between the first and the second side surfaces 22c,d. The top surface 22a of the head portion 20 and the first side surface 22c of the head portion 20 are perpendicular. Similarly, the second side surface 22d, the third side surface 22e, and the fourth side surface 22f are perpendicular to the top surface 22a.

The top surface 22a has four edges 23a-d. The first side surface 22c extends downward from a first one of the edges 23a towards the bottom surface 22b. Similarly, the second side surface 22d extends downward from a second one of the edges 23b towards the bottom surface 22b, the third side surface 22e extends downward from a third one of the edges 23c towards the bottom surface 22b, and the fourth side surface 22f extends downward from a fourth one of the edges 23d towards the bottom surface 22b.

Figure 1F:
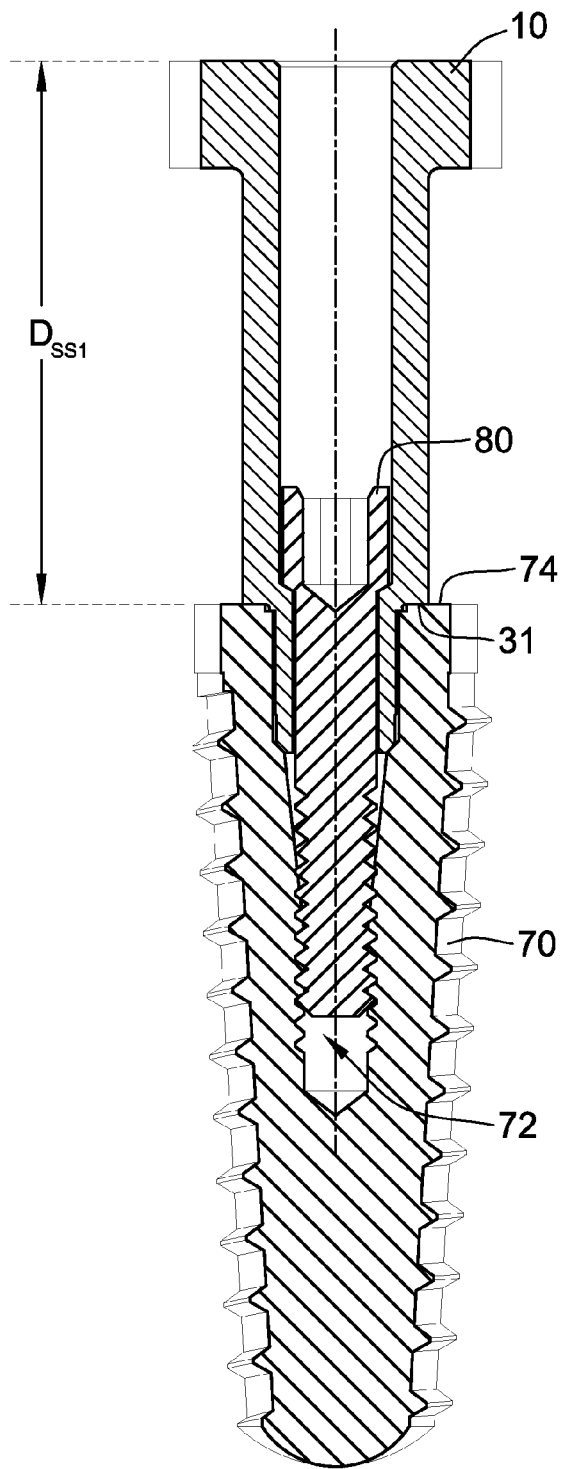
FIG. 1F is a side cross-sectional view of the scanning member of FIG. 1A coupled with the dental implant of FIG. 1E.
Figure 2A:
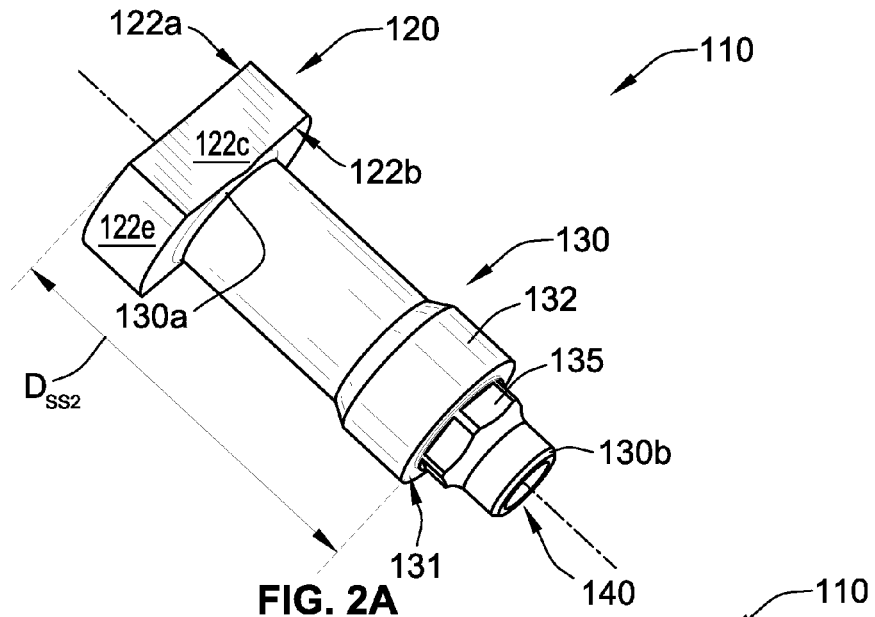
FIG. 2A is a perspective view of a second scanning member according to the present disclosure.
Figure 2C:
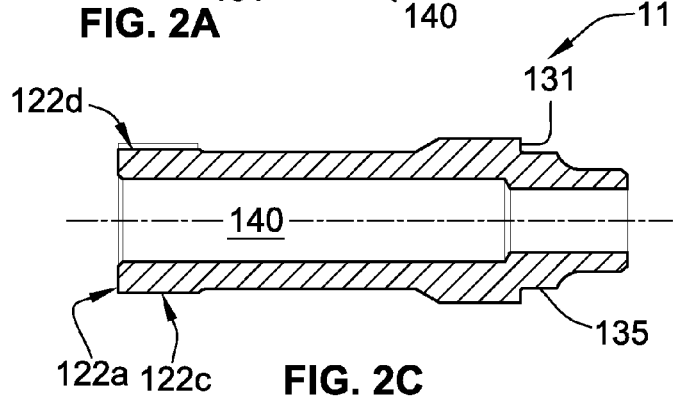
FIG. 2C is a cross-sectional side view of the scanning member of FIG. 2B.
Figures 2B, 2D:
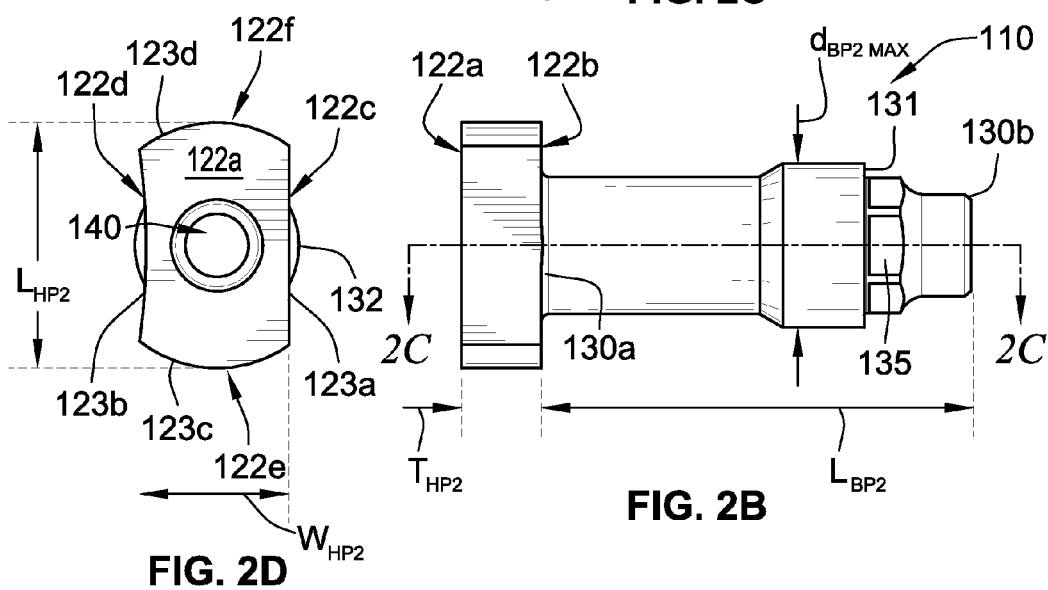
FIG. 2B is a side view of the scanning member of FIG. 2A.
FIG. 2D is a top view of the scanning member of FIG. 2A.

A proximal end 30a of the body portion 30 extends from the head portion 20 in a shaft like manner and terminates at a distal end 30b with a non-rotational feature 35. As shown in FIGS. 1E and 1F, the non-rotational feature 35 is configured to non-rotationally couple to a complimentary non-rotational feature 76 of a dental implant 70 (or a dental implant analog). In the non-limiting example shown, the non-rotational feature 35 of the scanning member 10 is an external non-rotational boss feature and the non-rotational feature 76 of the dental implant 70 is an internal non-rotational socket feature; however, as will be explained below in reference to FIGS. 3A-F, the boss and socket can be reversed such that the scanning member includes an internal non-rotational socket feature and the dental implant includes an external non-rotational boss feature.

The body portion 30 further includes a lip surface 31 that is configured to abut and/or rest upon a supporting surface 74 of the dental implant 70. Thus, when the scanning member 10 is fully engaged with and/or coupled to the dental implant 70, the non-rotational feature 35 of the scanning member 10 is fully inserted into the non-rotational feature 76 of the dental implant 70 such that the lip surface 31 contacts/touches the supporting surface 74.

The top surface 22a is configured to indicate a first characteristic of the dental implant 70 used in developing a custom-abutment (not shown) for attachment to the dental implant 70. The top surface 22a is substantially flat and located a predetermined distance, $D_{SS1}$, from the lip surface 31. Additionally, the substantially flat top surface 22a of the scanning member 10 is positioned such that the top surface 22a is parallel with the lip surface 31 of the scanning member 10 and with the supporting surface 74 of the dental implant 70 when the scanning member 10 is coupled to the dental implant 70. Thus, when the scanning member 10 is coupled to the dental implant 70, the top surface 22a is located the predetermined distance, $D_{SS1}$, from the support surface 74. As such, the top surface 22a indicates the location of the support surface 74 of the dental implant 70 (the first characteristic of the dental implant) when the scanning member 10 is coupled to the dental implant 70. It is noted that in the case of a model being used with a dental implant analog therein, the scanning member 10 is coupled to the dental implant analog and the top surface 22a indicates the location of a support surface of the dental implant analog in the same manner.

The first side surface 22c is configured to indicate a second characteristic of the dental implant 70 used in developing the custom-abutment (not shown). As best shown in FIGS. 1D and 1E, the first side surface 22c is the only one of the four side surfaces 22c-f of the head portion 20 that is substantially flat. That is, the second, the third, and the fourth side surfaces 22d-f of the head portion 20 are curved surfaces or non-flat surfaces. Thus, the first side surface 22c can be readily distinguished by a scanning system (e.g., mechanical contact scanner, optical scanner, laser scanner) from the other three side surfaces 22d-f. It is contemplated that the curved second side surface 22d can be a concave surface, a convex surface, or a combination thereof. Similarly, the third and the fourth side surfaces can be concave surfaces, convex surfaces, or combinations thereof.

The substantially flat first side surface 22c and the non-rotational feature 35 of the scanning member 10 are positioned relative to each other such that the first side surface 22c is parallel with at least one side surface 35a of the non-rotational feature 35 of the scanning member 10 and with at least one corresponding side surface 76a of the complementary non-rotational feature 76 of the dental implant 70 when the scanning member 10 is coupled to the dental implant 70. As such, the first side surface 22c indicates the orientation (rotational position) of the non-rotational feature 76 when the scanning member 10 is coupled to the dental implant 70.

As shown in FIGS. 1B and 1D, the head portion 20 has a length, $L_{HP1}$, a width, $W_{HP1}$, and a thickness, $T_{HP1}$, and the body portion 30 has a length, $L_{BP1}$, and a maximum diameter, $d_{BP1\ MAX}$. The length, $L_{HP1}$, of the head portion 20 is larger than the width, $W_{HP1}$, which is larger than the thickness, $T_{HP1}$. The length, $L_{HP1}$, of the head portion 20 is also larger than the maximum diameter, $d_{BP1\ MAX}$, of the body portion 30 which causes the scanning member 10 to have the generally "T" shape (FIG. 1A).

The length, $L_{BP1}$, of the body portion 30 is designed such that (1) the top surface 22a is located the predetermined distance, $D_{SS1}$, from the lip surface 31, and (2) the head portion 20 does not interfere with adjacent teeth (not shown) in the mouth of the patient irrespective of the orientation (rotational position) of the non-rotational feature 76 of the dental implant 70. For example, if the length, $L_{BP1}$, of the body portion 30 is too small (e.g., smaller than a height of the adjacent teeth), the head portion 20 could prevent a proper connection between the scanning member 10 and the dental implant 70, which would result in determining incorrect characteristics of the dental implant 70 during the scanning of the scanning member 10. It is contemplated that the length, $L_{BP1}$, of the body portion 30 is at least about 6 millimeters, but preferably at least about 10 millimeters. It is further contemplated that the length of the body portion 30 from the proximal end 30a to the lip surface 31 is at least about 5 millimeters, but preferably at least about 8 millimeters.

As best shown in FIG. 1F, the scanning member 10 further includes an internal through hole 40 for receiving a screw 80 that threadably engages with a threaded bore 72 of the dental implant 70. The screw 80 removably couples the scanning member 10 to the dental implant 70 such that the lip surface 31 remains in contact with the supporting surface 74. Thus, when the scanning member 10 is scanned using one of the aforementioned scanning techniques, the top surface 22a is located precisely at the predetermined distance from the support surface 74.

Now referring to FIGS. 2A-2D, a scanning member 110 is shown according to aspects of the present disclosure. The scanning member 110 is similar to the scanning member 10 in that the scanning member 110 includes a head portion 120 with a top surface 122a having four edges 123a-d, a bottom surface 122b, a first side surface 122c, a second side surface 122d, a third side surface 122e, and a fourth side surface 122f; a body portion 130 with a proximal end 130a and a distal end 130b, a lip surface 131, a non-rotational feature 135; and an internal through hole 140, which are the same as, or similar to, respectively, the head portion 20 with the top surface 22a having the four edges 23a-d, the bottom surface 22b, the first side surface 22c, the second side surface 22d, the third side surface 22e, and the fourth side surface 22f; the body portion 30 with the proximal end 30a and the distal end 30b, the lip surface 31, the non-rotational feature 35; and the internal through hole 40 of the scanning member 10.

The scanning member 110 differs from the scanning member 10 in that the body portion 130 of the scanning member 110 includes a wide portion 132 to accommodate a larger and/or wider non-rotational feature 135, as compared to the non-rotational feature 35 of the scanning member 10. Thus, a maximum diameter, $d_{BP2\ MAX}$, of the scanning member 110 is larger than the maximum diameter, $d_{BP1\ MAX}$, of the scanning member 10. For example, the maximum diameter, $d_{BP2\ MAX}$, and the non-rotational feature 135 of the scanning member 110 are at least about 5 percent larger than the maximum diameter, $d_{BP1\ MAX}$, and the non-rotational feature 35 of the scanning member 10. Such a larger non-rotational feature 135 can be used to non-rotationally couple the scanning member 110 to a dental implant having a larger (greater diameter) corresponding non-rotational feature (not shown).

While a distal section of the body portion 130, including the wide portion 132 and the non-rotational feature 135, is different than a corresponding distal section of the body portion 30, the head portion 120 is substantially identical to the head portion 20. That is, a length, $L_{HP2}$, a width, $W_{HP2}$, and a thickness, $T_{HP2}$, of the head portion 120 are substantially identical to the length, $L_{HP1}$, the width, $W_{HP1}$, and the thickness, $T_{HP1}$ of the head portion 20. Additionally, the predetermined distance, $D_{SS2}$, from the top surface 122a to the lip surface 131 is identical to the predetermined distance, $D_{SS1}$, from the top surface 22a to the lip surface 31.

Now referring to FIGS. 3A-3F, a scanning member 210 is shown according to aspects of the present disclosure. The scanning member 210 is similar to the scanning member 10 in that the scanning member 210 includes a head portion 220 with a top surface 222a having four edges 223a-d, a bottom surface 222b, a first side surface 222c, a second side surface 222d, a third side surface 222e, and a fourth side surface 222f; a body portion 230 with a proximal end 230a and a distal end 230b, a lip surface 231, a non-rotational feature 235; and an internal through hole 240, which are the same as, or similar to, respectively, the head portion 20 with the top surface 22a having the four edges 23a-d, the bottom surface 22b, the first side surface 22c, the second side surface 22d, the third side surface 22e, and the fourth side surface 22f; the body portion 30 with the proximal end 30a and the distal end 30b, the lip surface 31, the non-rotational feature 35; and the internal through hole 40 of the scanning member 10.

The scanning member 210 differs from the scanning member 10 in that the body portion 230 of the scanning member 210 includes an internal non-rotational socket feature 235 to mate and/or couple to a dental implant 270 (FIGS. 3E and 3F) with an external non-rotational boss feature 276, as compared to the internal non-rotational socket feature 76 (FIG. 1E) of the dental implant 70. As best shown in FIG. 3F, the internal through hole 240 is configured to receive a screw 280 that threadably engages with a threaded bore 272 of the dental implant 270. The screw 280 removably couples the scanning member 210 to the dental implant 270 such that the lip surface 231 of the scanning member 210 remains in contact with a supporting surface 274 of the dental implant 270.

Figure 3E:
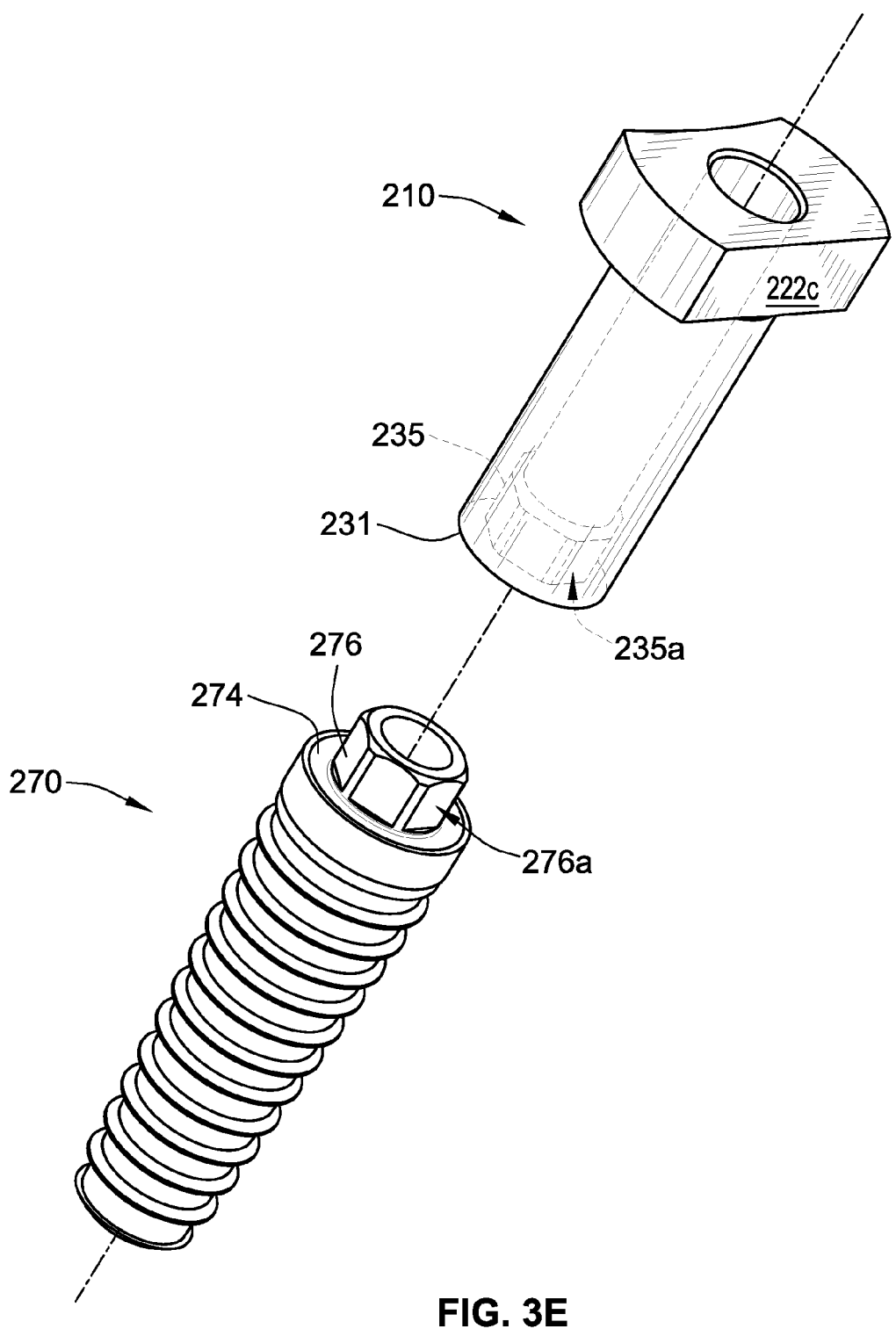
FIG. 3E is a perspective view of the scanning member of FIG. 3A aligned with a dental implant.
Figure 3F:
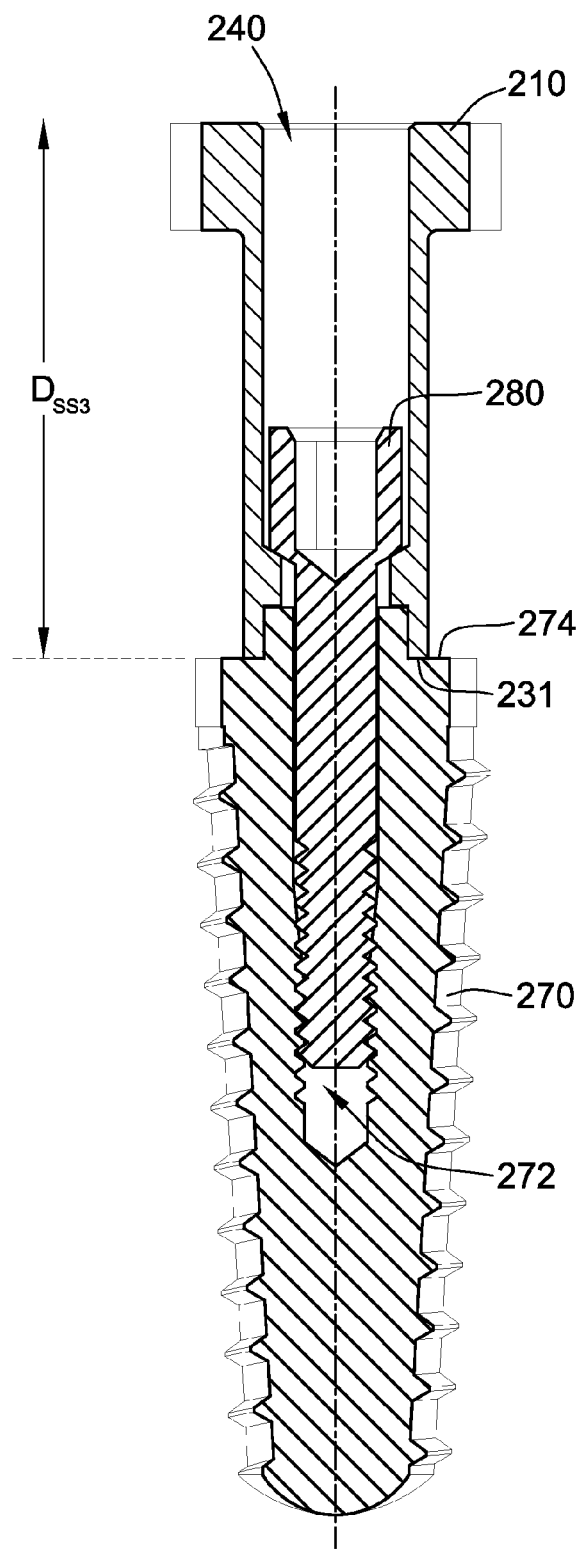
FIG. 3F is a side cross-sectional view of the scanning member of FIG. 3A coupled with the dental implant of FIG. 3E.

As best shown in FIG. 3E, the substantially flat first side surface 222c and the non-rotational feature 235 of the scanning member 210 are positioned relative to each other such that the first side surface 222c is parallel with at least one internal side surface 235a of the non-rotational feature 235 of the scanning member 210 and with at least one corresponding side surface 276a of the complementary non-rotational feature 276 of the dental implant 270 when the scanning member 210 is coupled to the dental implant 270. As such, the first side surface 222c indicates the orientation (rotational position) of the non-rotational feature 276 when the scanning member 210 is coupled to the dental implant 270.

While a distal section of the body portion 230, including the non-rotational feature 235, is different from a corresponding distal section of the body portion 30, the head portion 220 is substantially identical to the head portion 20. That is, a length, $L_{HP3}$, a width, $W_{HP3}$, and a thickness, $T_{HP3}$, of the head portion 220 are substantially identical to the length, $L_{HP1}$, the width, $W_{HP1}$, and the thickness, $T_{HP1}$ of the head portion 20. Additionally, the predetermined distance, $D_{SS3}$, (FIG. 3F) from the top surface 222a to the lip surface 231 is identical to the predetermined distance, $D_{SS1}$, from the top surface 22a to the lip surface 31. However, as the non-rotational feature 235 of the scanning member 210 is internal (socket) and not external (boss), the length, $L_{BP3}$, of the body portion 230 is less than the length, $L_{BP1}$, of the body portion 30 of the scanning member 10.

Now referring to FIGS. 4A-4D, a scanning member 310 is shown according to aspects of the present disclosure. The scanning member 310 is similar to the scanning member 10 in that the scanning member 310 includes a head portion 320 with a top surface 322a having four edges 323a-d, a bottom surface 322b, a first side surface 322c, a second side surface 322d, a third side surface 322e, and a fourth side surface 322f; a body portion 330 with a proximal end 330a and a distal end 330b, a lip surface 331, a non-rotational feature 335; and an internal through hole 340, which are the same as, or similar to, respectively, the head portion 20 with the top surface 22a having the four edges 23a-d, the bottom surface 22b, the first side surface 22c, the second side surface 22d, the third side surface 22e, and the fourth side surface 22f; the body portion 30 with the proximal end 30a and the distal end 30b, the lip surface 31, the non-rotational feature 35; and the internal through hole 40 of the scanning member 10.

The scanning member 310 differs from the scanning member 10 in that the body portion 330 of the scanning member 310 includes a wide portion 332 to accommodate a larger and/or wider non-rotational feature 335, as compared to the non-rotational feature 35 of the scanning member 10. Thus, a maximum diameter, $d_{BP4\ MAX}$, of the scanning member 310 is larger than the maximum diameter, $d_{BP1\ MAX}$, of the scanning member 10. Additionally, the scanning member 310 differs from the scanning member 10 in that the body portion 330 of the scanning member 310 includes an internal non-rotational socket feature 335 to mate and/or couple to a dental implant (not shown) with an external non-rotational boss feature, as compared to the internal non-rotational socket feature 76 (FIG. 1E) of the dental implant 70.

While a distal section of the body portion 330, including the non-rotational feature 335, is different than a corresponding distal section of the body portion 30, the head portion 320 is substantially identical to the head portion 20. That is, a length, $L_{HP4}$, a width, $W_{HP4}$, and a thickness, $T_{HP4}$, of the head portion 320 are substantially identical to the length, $L_{HP1}$, the width, $W_{HP1}$, and the thickness, $T_{HP1}$ of the head portion 20. Additionally, the predetermined distance, $D_{SS4}$, (FIG. 4A) from the top surface 322a to the lip surface 331 is identical to the predetermined distance, $D_{SS1}$, from the top surface 22a to the lip surface 31. However, as the non-rotational feature 335 of the scanning member 310 is internal (socket) and not external (boss), the length, $L_{BP4}$, of the body portion 330 is less than the length, $L_{BP1}$, of the body portion 30 of the scanning member 10.

Figure 5:
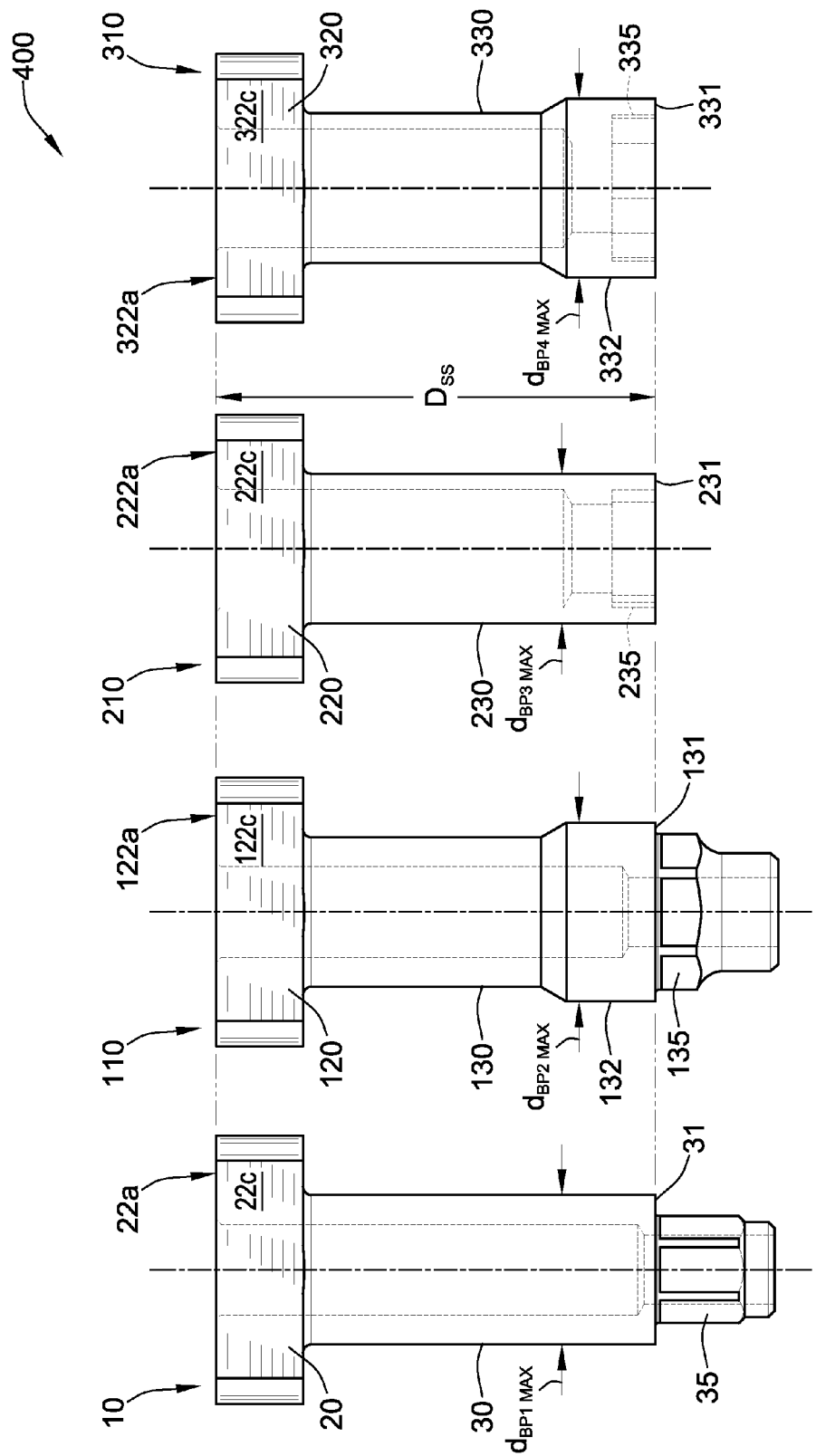
FIG. 5 is a side view of a set of scanning members according to the present disclosure.

Now referring to FIG. 5, a set of scanning members 400 is shown according to some aspects of the present disclosure. The set 400 can be packaged together for a clinician or laboratory technician to select a scanning member based on a determination of what manufacturer, type, and/or size of dental implant is installed in the mouth of a patient being treated. The clinician selects the appropriate scanning member having the non-rotational feature that is configured to mate with the complimentary non-rotational feature of the installed dental implant.

The set 400 includes the scanning members 10, 110, 210, and 310 described above. Where like reference numbers are used to describe like elements, the first scanning member 10 includes the first head portion 20 and the first body portion 30 having the first non-rotational feature 35, where the first non-rotational feature 35 is an external non-rotational boss feature. Similarly, the second scanning member 110 includes the second head portion 110 and the second body portion 130 having the second non-rotational feature 135, where the second non-rotational feature 135 is an external non-rotational boss feature. Additionally, the third scanning member 210 includes the third head portion 220 and the third body portion 230 having the third non-rotational feature 235, where the third non-rotational feature 235 is an internal non-rotational socket feature, and the fourth scanning member 310 includes the fourth head portion 320 and the fourth body portion 330 having the fourth non-rotational feature 235, where the fourth non-rotational feature 335 is an internal non-rotational socket feature.

The first body portion 30 has a first maximum diameter, $d_{BP1\ MAX}$, and the second body portion 130 has a second maximum diameter, $d_{BP2\ MAX}$, that is greater than the first maximum diameter, $d_{BP1\ MAX}$. Similarly, the third body portion 230 has a third maximum diameter, $d_{BP3\ MAX}$, and the fourth body portion 330 has a fourth maximum diameter, $d_{BP4\ MAX}$, that is greater than the third maximum diameter, $d_{BP3\ MAX}$. The variously sized scanning members in the set 400 can be configured to couple to variously sized dental implants supplied by one or more different manufacturers with different types of non-rotational features and/or different sizes (e.g., diameters).

The first scanning member 10 is configured to be non-rotationally coupled to a first dental implant. Similarly, the second scanning member 110 is configured to be non-rotationally coupled to a second dental implant, the third scanning member 210 is configured to be non-rotationally coupled to a third dental implant, and the fourth scanning member 310 is configured to be non-rotationally coupled to a fourth dental implant.

As described above, while the distal sections of the body portions 30, 130, 230, and 330 are different, the head portions 20, 120, 220, and 320 are substantially identical and the distance, $D_{SS}$, from the top surfaces 22a, 122a, 222a, and 322a to the lip surfaces 31, 131, 231, and 331 are substantially identical for each of the scanning members 10, 110, 210, and 310. No matter which one of the scanning members 10, 110, 210, and 310 is selected and used by the clinician or laboratory technician, the top surface 22a, 122a, 222a, and 322a is located the same distance, $D_{SS}$, away from the supporting surface of the dental implant, and the first side surface 22c, 122c, 222c, and 322c is parallel with at least one side surface (e.g., side surfaces 76a and 276a) of the non-rotational feature of the dental implant. Thus, each one of the scanning members 10, 110, 210, and 310 is configured to indicate two characteristics of a dental implant coupled thereto in the same manner as described herein.

Each one of the scanning members 10, 110, 210, and 310 in the set 400 is configured to be scannable via a mechanical contact scanner, via an optical scanner, and via a laser scanner to determine the two characteristics for use in developing a custom-abutment (not shown).

It is contemplated that the first, the second, the third, and the fourth dental implants are each made by a different manufacturer. Thus, in some aspects of the present disclosure, each of the scanning members 10, 110, 210, and 310 in the set 400 is configured to be coupled with a different dental implant provided by different manufacturers. It is also contemplated that each manufacturer uses a different connection, such as, for example, each manufacture may use a different type or size non-rotational feature (e.g., octagon, hexagon, lobe, etc.).

Now, several methods according to aspects of the present disclosure will be described. The scanning members of the present disclosure are used to provide information about a dental implant in a mouth of a patient or a dental implant analog in a model of the mouth. The information is used to develop or construct a custom-abutment that is attached to the dental implant such that a prosthetic tooth is properly aligned in the mouth of the patient.

As described above, after the dental implant is installed and the mouth of a patient has healed, a gingival end of the dental implant is exposed. A clinician can then determine a type of the dental implant in the mouth of the patient (e.g., manufacturer). Based on the determined type of dental implant, the clinician can select the corresponding type of scanning member (e.g., scanning members 10, 110, 210, and 310) from a set of scanning members (e.g., set 400). The clinician or laboratory technician then attaches the selected scanning member to the dental implant in the mouth of the patient.

After the scanning member is attached/installed to the dental implant in the mouth of the patient, any of the above mentioned techniques for scanning the scanning member directly in the mouth of the patient can be employed, such as, for example, optical scanning and laser scanning. The scanning of the scanning member generates scan data which is analyzed by a communicatively connected computer and/or software program to determine and/or gather information including a first characteristic and a second characteristic of the dental implant for use in manufacturing a custom-abutment. Specifically, the computer and/or software program determines the distance from a top surface of the scanning member to the supporting surface of the dental implant and the rotational position of a non-rotational feature of the dental implant. Based on the gathered information and characteristics, the custom abutment is developed using known methods, such as, for example, computer aided design (CAD) machines, mills, etc. The orientation of the non-rotational feature of the dental implant is needed because the lower portion of the developed custom-abutment must mate with the non-rotational feature of the dental implant such that the prosthesis is aligned with the adjacent teeth in the mouth. If the orientation is unknown or incorrect, the developed custom-abutment, after being installed, might not align with the adjacent teeth, which can give the undesirable appearance of a crooked tooth.

While the previous method involved scanning the mouth of a patient directly, the following method employs the use of a model of the mouth of the patient including an implant analog as described above. A scanning member, according aspects of the present disclosure, is non-rotationally attached to a dental implant analog in a model (e.g., stone or plaster model). The model and attached scanning member are scanned using one of the aforementioned scanning techniques (e.g., mechanical contact scanning, optical scanning, laser scanning) to generate scan data. A communicatively connected computer and/or software program creates a virtual three-dimensional image of the patient's dental conditions with the scan data. The computer and/or software program further determines and/or gathers information including the distance from a top surface of the scanning member to the supporting surface of the dental implant analog and the rotational position of a non-rotational feature of the dental implant analog for use in manufacturing a custom-abutment. The computer and/or software develops custom-abutment dimensional information based on the virtual three-dimensional image and the gathered information. The custom abutment is fabricated using the custom-abutment dimensional information using known methods, such as, for example, computer aided design (CAD) machines, mills, etc.

While the non-rotational features 35, 135, 235, and 335 are included in the scanning members 10, 110, 210, and 310 as being hexagonal features, it is contemplated that the non-rotational features 35, 135, 235, and 335 can have any polygonal shape, such as, for example, triangular, square, rectangular, pentagonal, etc., or non-round shape, such as, for example, lobe shape. In fact, the set of scanning members 400 shown in FIG. 5 may have some scanning members with different shaped connections.

While the top surface 22a, 122a, 222a, and 322a is shown and described as being substantially flat and parallel with the lip surface 31, 131, 231, and 331 to indicate the first characteristic of the dental implant (e.g., dental implant 70), it is contemplated that the top surface 22a, 122a, 222a, and 322a can indicate the first characteristic in other manners. For example, only a portion of the top surface 22a, 122a, 222a, and 322a may be flat while the rest is not.

While the first side surface 22c, 122c, 222c, and 322c is shown and described as being substantially flat and parallel with the at least one side surface 35a, 335a to indicate the second characteristic of the dental implant (e.g., dental implant 70) when the scanning member 10, 210 is coupled to the dental implant 70, 270, it is contemplated that the first side surface 22c, 122c, 222c, and 322c can indicate the second characteristic in other manners. For example, only a portion of the first side surface 22c, 122c, 222c, and 322c may be flat while the rest is not.

While the first, the second, the third, and the fourth side surfaces 22c-f, 122c-f, 222c-f, and 322c-f are shown and described as being perpendicular to the top surface 22a, 122a, 222a, and 322a, various other arrangements are contemplated. For example, in some aspects of the present disclosure only the first side surface 22c, 122c, 222c, and 322c may be perpendicular to the top surface 22a, 122a, 222a, and 322a, or at least a portion of the first side surface 22c, 122c, 222c, and 322c may be perpendicular to the top surface 22a, 122a, 222a, and 322a. In such alternatives implementations, one or more of the second, the third, and the fourth side surfaces 22d-f, 122d-f, 222d-f, and 322d-f may be slanted at one or more angles with respect to the top surface 22a, 122a, 222a, and 322a.

While the set 400 is shown and described as including four scanning members, various other numbers and combinations of scanning members are contemplated. For example, the set 400 can include two or more scanning members according to aspects of the present disclosure. For another example, the set 400 can include ten or more scanning members according to aspects of the present disclosure. For yet another example, the set 400 can include one or more of the first scanning member 10, one or more of the second scanning member 110, one or more of the third scanning member 210, and/or one or more of the fourth scanning member 310.

It is contemplated that alphanumeric identification or identifiers can be included on any of the scanning members of the present disclosure to identify the manufacturer of the dental implant that the scanning member is configured to be coupled to and/or the size of such dental implant. For example, a scanning member can include the text "Biomet 3i, 3.4 mm" on the body portion to indicate that the scanning member is configured to be coupled to a Biomet 3i dental implant having a 3.4 mm size. The alphanumeric identifier can be printed or laser etched onto the scanning member by any known method.

It is contemplated that the scanning members of the present disclosure are reusable scanning members. That is, the scanning members of the present disclosure can be sterilized using various methods, such as, for example, using an autoclave.

While the scanning members of the present disclosure have been described relative to use with a single dental implant, two or more of the scanning members of the present disclosure can be used with multiple dental implants in a mouth of a patient at once. For example, in a mouth having two dental implants installed therein, two scanning members according to aspects of the present disclosure can be attached to the dental implants in the mouth (or attached to two dental implant analogs in a model of the mouth) and scanned according to one of the aforementioned scanning methods. The generated scan data for both of the scanning members can be used together to create or develop a bar that is attached to the two dental implants. The bar is configured to receive a denture structure such as shown in U.S. Pat. No. 6,382,975, which is hereby incorporated by references herein in its entirety.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the present disclosure, which is set forth in the claims that follow.

What is claimed is:

1. A method of developing a custom-abutment for attachment to a dental implant in a mouth of a patient, comprising:
   determining a type of the dental implant in the mouth of the patient;
   selecting a scanning member from a set of scanning members based on the determined type of the dental implant, each of the scanning members in the set having a head portion coupled to a body portion, the head portions being identical for each of the scanning members in the set, the body portions being different for each of the scanning members in the set, the body portions each having a non-rotational feature that is configured to be coupled with a different type of non-rotational dental implant feature, the head portion having (i) a top surface indicative of a first characteristic of the dental implant, (ii) a first side surface that is substantially flat and indicative of a second characteristic of the dental implant, the first side surface of the head portion being parallel with at least one side surface of the non-rotational feature of the body portion, and (iii) a second side surface that is curved for aiding in distinguishing the second side surface from the first side surface, the second side surface opposing the first side surface;
   attaching the selected one of the scanning members to the dental implant in the mouth of the patient;
   determining, via scanning the head portion of the attached scanning member, the first characteristic and the second characteristic of the dental implant to gather information for manufacturing the custom-abutment; and developing the custom abutment based on the information from the first characteristic and the second characteristic of the attached scanning member.

2. The method of claim 1, wherein the top surface of the head portion is substantially flat.

3. The method of claim 2, wherein the top surface of the head portion and the first side surface of the head portion are perpendicular.

4. The method of claim 3, wherein the second side surface that opposes the first side surface is perpendicular to the top surface.

5. The method of claim 1, wherein the top surface of the head portion is located a predetermined distance above a support surface of the dental implant, the first characteristic being the location of the support surface of the dental implant.

6. The method of claim 5, wherein the predetermined distance is about 10 millimeters.

7. The method of claim 1, wherein the different types of non-rotational dental implant features include internal non-rotational socket features and external non-rotational boss features.

8. The method of claim 1, wherein the different types of non-rotational dental implant features are provided by different manufacturers of dental implants.

9. The method of claim 1, wherein each of the scanning members in the set is configured to be coupled with a different dental implant provided by different manufacturers.

10. The method of claim 1, wherein the determining the type of the dental implant includes determining whether a gingival end of the dental implant has an internal non-rotational socket feature or an external non-rotational boss feature.

11. The method of claim 10, wherein the determining the type of the dental implant further includes determining a diameter of the internal non-rotational socket feature or the external non-rotational boss feature.

12. The method of claim 1, wherein the first characteristic provides information regarding a location of a supporting surface of the dental implant and wherein and the second characteristic provides information regarding an orientation of a non-rotational feature of the dental implant.

13. The method of claim 1, wherein the head portion has a length, a width, and a thickness, the length of the head portion being greater than a maximum diameter of the body portion.

14. The method of claim 13, wherein the body portion of the attached scanning member has a length such that the head portion does not interfere with adjacent teeth in the mouth of the patient irrespective of the orientation of the non-rotational feature of the dental implant.

15. A method of developing a custom-abutment for attachment to a dental implant in a mouth of a patient, comprising:
    non-rotationally coupling a scanning member to the dental implant in the mouth of the patient, the scanning member having a head portion coupled to a body portion which forms a generally "T" shape, the body portion having a non-rotational feature, the head portion having (i) a top surface indicative of a first characteristic of the dental implant, (ii) a first side surface that is substantially flat and indicative of a second characteristic of the dental implant, the first side surface of the head portion being parallel with at least one side surface of the non-rotational feature of the body portion, and (iii) a second side surface that is curved for aiding in distinguishing the second side surface from the first side surface, the second side surface opposing the first side surface;
    scanning at least a portion of the mouth of the patient to create scan data, the portion of the mouth including the scanning member;
    analyzing the scan data to determine the first characteristic and the second characteristic of the dental implant for use in manufacturing the custom-abutment; and
    developing the custom abutment based on the scan data, the first characteristic, and the second characteristic.

16. The method of claim 15, wherein the top surface of the head portion is substantially flat and wherein the top surface is perpendicular to the first side surface.

17. The method of claim 16, wherein the second side surface that opposes the first side surface is perpendicular to the top surface.

18. The method of claim 15, wherein the first characteristic provides information regarding a location of a support surface of the dental implant and wherein and the second characteristic provides information regarding an orientation of a non-rotational feature of the dental implant.

19. A method of manufacturing a custom dental abutment for mating with a dental implant, comprising:
    scanning a model of a patient's dental conditions, the model including a dental implant analog, teeth models, and a scanning member having a head portion coupled to a body portion, the scanning member having a generally "T" shape, the body portion having a non-rotational feature that is configured to be non-rotationally coupled to the dental implant analog, the head portion having (i) a top surface indicative of a first characteristic of the dental implant analog, (ii) a first side surface that is substantially flat and indicative of a second characteristic of the dental implant analog, the first side surface of the head portion being parallel with at least one side surface of the non-rotational feature of the body portion, and (iii) a second side surface that is curved for aiding in distinguishing the second side surface from the first side surface, the second side surface opposing the first side surface;
    generating scan data from the scanning of the model;
    creating a virtual three-dimensional image of the patient's dental conditions with the scan data;
    determining the first characteristic and the second characteristic of the dental implant analog to gather information for manufacturing the custom-abutment;
    developing custom-abutment dimensional information based on the virtual three-dimensional image and the information gathered; and
    fabricating the custom-abutment utilizing the custom-abutment dimensional information.

20. The method of claim 19, further including, prior to the scanning, (i) taking an impression of the patient's dental conditions and (ii) preparing the model based on the impression.

21. The method of claim 20, further including, prior to the scanning, attaching the scanning member to the dental implant analog.

22. The method of claim 19, wherein the head portion is configured to be scannable via a mechanical contact scanner and via an optical scanner to generate the scan data for use in determining the first characteristic and the second characteristic of the dental implant analog.

* * * * *

UNITED STATES PATENT AND TRADEMARK OFFICE
CERTIFICATE OF CORRECTION

| | | |
|---|---|---|
| PATENT NO. | : 8,882,508 B2 | Page 1 of 1 |
| APPLICATION NO. | : 13/312900 | |
| DATED | : November 11, 2014 | |
| INVENTOR(S) | : John J. Bellanca et al. | |

It is certified that error appears in the above-identified patent and that said Letters Patent is hereby corrected as shown below:

On the Title Page, Item (75), for Inventor David Edward Beeby, please delete the city "Wotton-Under-Edge" and insert --Gloucestershire --, therefor.

Signed and Sealed this
Fourteenth Day of April, 2015

Michelle K. Lee
*Director of the United States Patent and Trademark Office*